United States Patent
Anderson et al.

(10) Patent No.: US 6,939,674 B2
(45) Date of Patent: Sep. 6, 2005

(54) MEDICINE RESPONSE ASSAY IN RESPIRATORY DISEASE

(75) Inventors: Wayne H. Anderson, Durham, NC (US); Lisa D. Edwards, Durham, NC (US); Amanda H. Emmett, Durham, NC (US); Sreekumar Pillai, Durham, NC (US); Catherine S. Sprankle, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 339 days.

(21) Appl. No.: 10/240,305
(22) PCT Filed: Apr. 17, 2001
(86) PCT No.: PCT/US01/12534
§ 371 (c)(1), (2), (4) Date: Sep. 30, 2002
(87) PCT Pub. No.: WO01/79560
PCT Pub. Date: Oct. 25, 2001

(65) Prior Publication Data
US 2003/0162193 A1 Aug. 28, 2003

Related U.S. Application Data
(60) Provisional application No. 60/236,608, filed on Sep. 29, 2000, and provisional application No. 60/197,913, filed on Apr. 17, 2000.

(51) Int. Cl.[7] .................. C12Q 1/68; C12P 19/34; C07H 21/04
(52) U.S. Cl. .................. 435/6; 435/91.1; 435/91.2; 536/23.1; 536/24.3; 536/24.33
(58) Field of Search .................. 435/6; 536/23.1; 514/11

(56) References Cited

U.S. PATENT DOCUMENTS
6,334,099 B1 * 12/2001 Grace et al. .................. 702/194

FOREIGN PATENT DOCUMENTS
WO WO 97/42347 * 11/1997
WO WO 99/10529 * 3/1999

OTHER PUBLICATIONS

Silverman et al. Pharmacogenetics of the 5' lipoxygenase Pathway in Asthma et al. Clinical and Experimental Allergy, 1998, vol. 28, Supplemental 5, pp. 164–170, 1998.*

Calhoun, "Anti–leukotrienes for asthma," *Current Opinion in Pharmacology* 1(3):230–234 (Jun. 2001).

Drazen et al., "Pharmacogenetic association between ALOX5 promoter genotype and the response to anti–asthma treatment," *Nature Genetics* 22(2):168–170 (Jun. 1999).

In et al., "Naturally occurring mutations in the human 5–lipoxygenase gene promoter that modify transcription factor binding and reporter gene transcription," *Journal of Clinical Investigation* 99(5):1130–1137 (1997).

Sanak et al., "Leukotriene C4 synthase promoter polymorphism and risk of aspirin–induced asthma," *Lancet* 350(9091):1599–1600 (Nov. 1997).

Silverman et al., "Pharmacogenetics of the 5–lipoxygenase pathway in asthma," *Clinical and Experimental Allergy* 28(Suppl. 5):164–170 (Nov. 1998).

* cited by examiner

Primary Examiner—Kenneth R. Horlick
Assistant Examiner—Cynthia Wilder
(74) Attorney, Agent, or Firm—Virginia G. Campen

(57) ABSTRACT

Correlations between polymorphisms in the 5-lipoxygenase gene, or polymorphisms in the leukotriene C4 synthase gene, and a subject's phenotypic response to treatment with a leukotriene receptor antagonist for respiratory disease are described. Methods of screening subjects to aid in treatment, and methods of screening therapeutic compounds, are presented.

6 Claims, 4 Drawing Sheets

SEQUENCE LISTING

```
<160> NUMBER OF SEQ ID NOS: 16
<210> SEQ ID NO 1
<211> LENGTH: 4465
<212> TYPE: DNA
<213> ORGANISM: Homo sapiens
<220> FEATURE:
<221> NAME/KEY: CDS
<222> LOCATION: (1447)..(1504)
<220> FEATURE:
<221> NAME/KEY: CDS
<222> LOCATION: (2950)..(3049)
<220> FEATURE:
<221> NAME/KEY: CDS
<222> LOCATION: (3152)..(3222)
<220> FEATURE:
<221> NAME/KEY: CDS
<222> LOCATION: (3307)..(3388)
<220> FEATURE:
<221> NAME/KEY: CDS
<222> LOCATION: (3619)..(3757)
```

```
<400> SEQUENCE: 1
gagctcacag agcccccagc tgggcatat  ctggtttccg ggggcagggg cgatacccag      60
aggaggaaga agggattctg agagagccca acaggctccg agcctcaggc tggagctgag    120 cttgggcag  caaggaagga ccaggtgcga gggcagaacc atgcggcccg acccctgcag    180
cacggcctgt ggcctccccc agctcctgcc cgtgcttctg ggtcagtctg actttgcca    240 cttctgacca aaagccaccg caaacccact caagccaaaa gaggaagtga ccgttaggcc    300
caactgggaa ggctggcggc caggggcact ccaggcaggg cgagggggc ggccggggc     360 gctccaggcg gggcgaggga gacacccaga actccaggca ggagtcctcg ggtgccacct    420
ttcctctcca cctggccctg cgtgggctct gtcctcaggg tggcccgccg tagtcccct     480 ccccactctg agtttcctgt cccaaagtcc taaggaagtt tccagaacta catctcacca    540
tcttgagtca gccttggctc agtgtccatc tcacaggcct ggaagggca ggagtcagca     600 ctgtccagac cacagggcct gagtgtgggg agggcagccg tctaggaagg tggtggaggg    660
ttgttacctt gaggcaagag ggctgcgggg cagaaagaca cagcaggtga ctgttgtggg    720
aggcccaaga gaggcctggg agagggatgg cccacaaggg ctgaccctcc cgccacccag    780
ggggccttgg acaggttcc tcctggcagg gtggcccttg tgcatggaac ccctacaacg     840
actaaggctg gcaggcatga ggtttcctga aggagaaaga gcttgtgggg cccagtgtgg    900 ctggggggc gctgggactc cattctgaag ccaaaggcac tgggaagggc ttccgcagag     960
gagggtttgg caggggttgc caggaacagc tggatgggg acaggaaca gataaggtgg    1020 gtggaggagt tagccgggag cctggggctg gctccagcat gatgtggggg tctgcaaggc   1080
cctggagaaa gtgggtggt gcagcagggg gcacacccac agctggagct gacccagatg    1140
gacagcttgg gctctgccac gcgggactag gcaaggaagg ggcacgaaca agcaggaagt   1200
ggtgaggcgg tctccagcta gctgctctcc cctgcccaga cttggttttc ctccctgctg   1260
gcttggcctg gctccctggc tctgtgtggt atggtcacac cccgtgcac cctccact      1320 gagatggggc ggggagagca ccgaggctgc tcttcctctc ctgggccgtc tctgagcag     1380 cagacggggc taagcgttcc ccagctcgcc ttcacacaca gcccgtgcca ccacaccgac    1440 ggtacc atg aag gac gag gta gct cta ctg gct gct gtc acc ctc ctg      1488
       Met Lys Asp Glu Val Ala Leu Leu Ala Ala Val Thr Leu Leu
       1               5                  10
```

-continued

```
gga gtc ctg ctg caa g gtgggctggt tcctatctag aagagggtg ggccttagat    1544
Gly Val Leu Leu Gln
 15 ccctacagct tgccctctgc ccctaggcc caggtggagg cagaggtgg ggactccagc    1604 ccaggcccaa gctggaagag ggtggggact tcagggaac tgggggcac ctggctgtga    1664 gagctgtagg acttgggggt ggcaagggtg ccaggacaaa tggtaggata gccatgggct    1724 tggggaagct gatctctgct ctttccagct gtccctctc tgggcgtccc agcaagcggc    1784 ccccattccc tggctctgct tcaaaggcac ctccatactg gaccacgtg agcagggta    1844 gaggtgggac tccttcctcc agccccctaa aaagagcctg cttaatgcct ttctcagact    1904 ggccctaaag gacacattcc ttggccagat atccttgcca cctaagagac accactactc    1964 cacagtgtgt gggctaggat aaggcacagc ctggggaggg ggctctgaag gggctgaaca    2024 gacaggccag cctgacctcc agctgctcct gcactgagct ggatggccac cctgtgacac    2084 ccatctgcag agggcccaga accaaaggtg ccagggctgc aggactcagg gggagatggt    2144 ccgacgggag gtctggggag ggagcgcaca gccagcactg gtctgtgtgt ggtctggcct    2204 ggcctcacct gaccaagaga agggctcctg cccacagaga aactttaggg ccagcccacc    2264 ctctgcaact accccagccc tggggtcctg gggttaggct aggagagtcc cagctgcaac    2324 ctcctgggag caggagagaa ggtgtctgtc agatttaggc ctgggaccgg aatgcaggaa    2384 cagagaaact gaggtttgga ggcacaggga cgcaggcttt agtgatcccg gcctgaggca    2444 gggtcagagg gccctgctgg tgggcgctgg taggtgggtg accagggact gttagctaca    2504 gggagtgtgc ttccttgcac ctgggaggat gcagccagct ctgccctcag actcccgagg    2564 cacttcctgg ccagggacct gaaagctgca tttgcctgtg ttttgagagt gaaatgattc    2624 agaaacaagg actcaagtgg tctctctcgc ggagcaggtg tccctgtgcc tgaatcactc    2684 accctccccc atacactcac aggttgggac agggcctctc tgcgcccag gcttcagccc    2744 tgccctcctc gctgaatgtc agggacacag ggcaggccag ggatgggtga cgagaggt    2804 ctcctcgggc ggggaggggg cggggttccg ccttagggag gagaggacac ggccaagtga    2864 agggccagat tgcaggatcc ctcccactcc catctctggg gcttcgggtg tccagacctg    2924 actcccgctc cccctcctcc cccag cc tac ttc tcc ctg cag gtg atc tcg    2975
                                Ala Tyr Phe Ser Leu Gln Val Ile Ser
                                 20              25 gcg cgc agg gcc ttc cgc gtg tcg ccg ccg ctc acc acc ggc cca ccc    3023
Ala Arg Arg Ala Phe Arg Val Ser Pro Pro Leu Thr Thr Gly Pro Pro
 30              35                  40 gag ttc gag cgc gtc tac cga gcc ca  gtgaggcgcg gcgggagggc    3069
Glu Phe Glu Arg Val Tyr Arg Ala Gln
 45              50 gcggggcggg gagcgagccc caggcgggtc cgggtcgcag gaccatcccg gccgcgcgc    3129 tcatcccacc cgcccaccgc ag g gtg aac tgc agc gag tac ttc ccg ctg    3179
                        Val Asn Cys Ser Glu Tyr Phe Pro Leu
                         55                  60 ttc ctc gcc acg ctc tgg gtc gcc ggc atc ttc ttt cat gaa g         3222
Phe Leu Ala Thr Leu Trp Val Ala Gly Ile Phe Phe His Glu
 65              70                  75 gtcgggtgt ggggcagggg cgcacgcgct ggaccccgg gacccgcgca gggcgctcac    3282
caggcccgtg cgtacctctc gcag gg  gcg gcg gcc ctg tgc ggc ctg gtc    3332
                               Gly Ala Ala Ala Leu Cys Gly Leu Val
                                80                  85
```

```
tac ctg ttc gcg cgc ctc cgc tac ttc cag ggc tac gcg cgc tcc gcg      3380
Tyr Leu Phe Ala Arg Leu Arg Tyr Phe Gln Gly Tyr Ala Arg Ser Ala
            90                  95                 100 cag ctc ag   gtgagggccg gcgggagc ggggcgggc cggggaaaga                3428
Gln Leu Arg tcgcgggcgg gcgggctcc tggggagcgg gaccgaagct gggggcgggc gacgggccgg      3488
agcccagcgc ctttggggat tcggtgggcg agccctggcg gcggccagag gaagtccccg     3548
tggggccagg gttgcggcgg ggaagaagcg ggcctcctcg cgccacctcc ccgctgaccg     3608
ccgcccgcag g ctg gca ccg ctg tac gcg agc gcg cgc gcc ctc tgg ctg     3658
             Leu Ala Pro Leu Tyr Ala Ser Ala Arg Ala Leu Trp Leu
             105                 110                 115 ctg gtg gcg ctg gct gcg ctc ggc ctg ctc gcc cac ttc ctc ccg gcc      3706
Leu Val Ala Leu Ala Ala Leu Gly Leu Leu Ala His Phe Leu Pro Ala
            120                 125                 130 gcg ctg cgc gcc gcg ctc ctc gga cgg ctc cgg acg ctg ctg ccg tgg      3754
Ala Leu Arg Ala Ala Leu Leu Gly Arg Leu Arg Thr Leu Leu Pro Trp
            135                 140                 145 gcc tgagaccaag gcccccgggc cgacggagcc gggaaagaag agccggagcc            3807
Ala
150 tccagctgcc ccggggaggg gcgctcgctt ccgcatccta gtctctatca ttaaagttct    3867 agtgaccgag acccgggctg cgttctctgg gtccgcgggg gtggcgcacc gcgggctacg    3927 gagcctggag gggcccagcc cgagtccggg cagcccgggg cgggcttcct agtggcggcg    3987 tgagagtggc tgcgaaggaa cgagccctcc ccctggggcg ggactggatc cggtcttcac    4047 ctcctacccc actccctact cagcctcggg gtcacaaggc cgcccagtcc tgccggggtt    4107 caccctccta gcgctcagcg gtctcctcac cggtccccct cctcagggc cttccctcga     4167 ctctcagccg ccgcagtccc tcgtcccctg gccttcacag ctgacactag atagagcctg    4227 tggctctctc cccaggtgag ggcagggatt tttcttttgg tcagcactgg atccccctcg    4287 ttaactgtag gtgttcaggg cagccctccg aggtccgcag agctgcgggc accatgggaa    4347 cgaagtgagt cagtgacagg cggtctcaag gaaatgtcca aagccttgg ggatccaggg     4407 gaggcccaca gaaacaaaga agtgactttt agccaagtat gcaggagaaa cggaggag     4465

<210> SEQ ID NO 2
<211> LENGTH: 150
<212> TYPE: PRT
<213> ORGANISM: Homo sapiens

<400> SEQUENCE: 2

Met Lys Asp Glu Val Ala Leu Leu Ala Ala Val Thr Leu Leu Gly Val
1               5                   10                  15

Leu Leu Gln Ala Tyr Phe Ser Leu Gln Val Ile Ser Ala Arg Arg Ala
            20                  25                  30

Phe Arg Val Ser Pro Pro Leu Thr Thr Gly Pro Pro Glu Phe Glu Arg
            35                  40                  45

Val Tyr Arg Ala Gln Val Asn Cys Ser Glu Tyr Phe Pro Leu Phe Leu
50                  55                  60

Ala Thr Leu Trp Val Ala Gly Ile Phe Phe His Glu Gly Ala Ala Ala
65                  70                  75                  80

Leu Cys Gly Leu Val Tyr Leu Phe Ala Arg Leu Arg Tyr Phe Gln Gly
            85                  90                  95

Tyr Ala Arg Ser Ala Gln Leu Arg Leu Ala Pro Leu Tyr Ala Ser Ala
            100                 105                 110
```

-continued

```
Arg Ala Leu Trp Leu Leu Val Ala Leu Ala Ala Leu Gly Leu Leu Ala
        115                 120                 125

His Phe Leu Pro Ala Ala Leu Arg Ala Ala Leu Leu Gly Arg Leu Arg
    130                 135                 140

Thr Leu Leu Pro Trp Ala
145                 150

<210> SEQ ID NO 3
<211> LENGTH: 20
<212> TYPE: DNA
<213> ORGANISM: Homo sapiens

<400> SEQUENCE: 3
ctggatgggg acagggaaca                                                 20

<210> SEQ ID NO 4
<211> LENGTH: 20
<212> TYPE: DNA
<213> ORGANISM: Homo sapiens

<400> SEQUENCE: 4
ctggatgggg accgggaaca                                                 20

<210> SEQ ID NO 5
<211> LENGTH: 2189
<212> TYPE: DNA
<213> ORGANISM: Homo sapiens

<400> SEQUENCE: 5
ggatccagaa taaccaaaac aatattgaaa aataaagaac agcgttggtg gattaacatt       60
ttccaatttc aaaacttact atagcactgc ggtaatcaag cagtgtggca ctgtatagca      120
tgtacattac agatcagtgg actagaatca atgtccagaa ataaaccgtt atgtttataa      180
tgaattactt tttaataagg tgtcaagaca acgcaatggg aaaagaataa tgaattcaac      240
aaatgatgca tggacaaccg gacatgcaca tgcaacacaa tgaatttgaa ttcttctatc      300
gctccatgca taaaaactaa ctcaaaatgg gtcacggatg taaatgaaaa gctaaaacta      360
taataatcct agaggaaaac ctaggagtaa atctttaaga tgttattgta ggcagtggtt      420
tctcagatag gaccccaaaa tcacaagcga caaaagaaa ttggacttaa agttaaatac      480
ttttgtgctt caaacatcat caagaaagtg aaaacacaac ccgcagaagc aataaaaatg      540
tctgtaagtc atgtatccga ttagagactt ctatccagga tatataaata atgcaattca      600
atgataaaaa agataaatag cccagttttc caaagagtca agcatctgaa tatacatctc      660
tccaaaaata tacagatatc caacaagcat gtgaaaagat gttcaaagcc atttgccagg      720
tgcacaaacc caagacagta tgaggagatg ctacagggac tctgctgctt cacagacatg      780
aagcgttggt gagaatgtag gcagccgcct ttggggactt cacatccccg ccgccccacg      840
cacggtgagc tagtgtttaa acttagccga gatcaataca cgcgactgtg tgcccgtcag      900
accctgcgct gccggcgggg ctgggagagg cgggcgccag gagtgggcgg gaacctgggg      960
gtcaggcccc agccgcggga agcgcgccca ggagcgcgcg aaaccttctc cacacccttc     1020
caggcatttg cccgccgcga ttcagagagc cgacccgtga ccctggcct ccctagaca      1080 gccccgcatg tccagatgtg ccgtcccgcc tgcctcccgc gaccactggc catctctggg     1140
cctgggcgcg gttctcggcg cccggcctgc ccccgccagg agccgcaggt ccagccagtg     1200
aagaagcccg cgcctgaagg agcctctgtg ctccagaatc catcctcagt atcagcgctg     1260
```

```
gggtggcctc ctccaggaag cccttctgat tctctcatgg gtcgctcttc ctctgcagac    1320
tcccggagca cccctgctc caagtaccgc aagtggcact gagaacttgg ggagagcaga    1380
ggctgtgcct agatttgtag ggagtccccg cagctccacc ccagggccta caggagcctg    1440
gccttgggcg aagccgaggc aggcaggcag ggcaaagggt ggaagcaatt caggagagaa    1500
cgagtgaacg aatggatgag gggtggcagc cgaggttgcc ccagtcccct ggctgcagga    1560
acagacacct cgctgaggag agacccagga gcgaggcccc tgccccgccc gaggcgaggt    1620
cccgcccagt cggcgccgcg cgtgaagagt gggagagaag tactgcgggg gcggggggcgg    1680 gggcggggc ggggggcgggg gcagccggga gcctggagcc agaccggggc ggggccggga    1740
ccggggccag ggaccagtgg tgggaggagg ctgcggcgct agatgcggac acctggaccg    1800
ccgcgccgag gctcccggcg ctcgctgctc ccgcggcccg cgccatgccc tcctacacgg    1860
tcaccgtggc cactgcagcc cagtggttcg ccggcactga cgactacatc tacctcagcc    1920
tcgtgggctc ggcgggctgc agcgagaagc acctgctgga caagcccttc tacaacgact    1980
tcgagcgtgg cgcggtgagc gcgggcgggg cacgggtgga gcgcgggctg aggtgcgtcc    2040
gggacccggt ttggacggca gaggcctggg cggggcgcc gagggcccgt cggggcggcc    2100
cggacaggac tggggtgtc caggaccctg tcagggaggg cagaactgcg gtggggcgtg    2160
ccctgggctc ccagtggccg gtgggtacc                                     2189

<210> SEQ ID NO 6
<211> LENGTH: 26
<212> TYPE: DNA
<213> ORGANISM: Artificial Sequence
<220> FEATURE:
<223> OTHER INFORMATION: ALOX5 forward primer

<400> SEQUENCE: 6
aggaacagac acctcgctga ggagag                                          26

<210> SEQ ID NO 7
<211> LENGTH: 26
<212> TYPE: DNA
<213> ORGANISM: Artificial Sequence
<220> FEATURE:
<223> OTHER INFORMATION: ALOX5 reverse primer

<400> SEQUENCE: 7
gagcagcgag cgccgggagc ctcggc                                          26

<210> SEQ ID NO 8
<211> LENGTH: 22
<212> TYPE: DNA
<213> ORGANISM: Artificial Sequence
<220> FEATURE:
<223> OTHER INFORMATION: LTC4S -444A probe

<400> SEQUENCE: 8
cctggatggg gacagggaac ag                                              22

<210> SEQ ID NO 9
<211> LENGTH: 20
<212> TYPE: DNA
<213> ORGANISM: Artificial Sequence
<220> FEATURE:
<223> OTHER INFORMATION: LTC4S - -444C probe

<400> SEQUENCE: 9
```

-continued

```
tggatgggga ccgggaacag                                                20
```

<210> SEQ ID NO 10
<211> LENGTH: 18
<212> TYPE: DNA
<213> ORGANISM: Artificial Sequence
<220> FEATURE:
<223> OTHER INFORMATION: LTC4S forward primer

<400> SEQUENCE: 10

```
tccgcagagg agggtttg                                                  18
```

<210> SEQ ID NO 11
<211> LENGTH: 21
<212> TYPE: DNA
<213> ORGANISM: Artificial Sequence
<220> FEATURE:
<223> OTHER INFORMATION: LTC4S reverse primer

<400> SEQUENCE: 11

```
gctaactcct ccacccacct t                                              21
```

<210> SEQ ID NO 12
<211> LENGTH: 6
<212> TYPE: DNA
<213> ORGANISM: Artificial Sequence
<220> FEATURE:
<223> OTHER INFORMATION: Sp1 binding site motif

<400> SEQUENCE: 12

```
gggcgg                                                                6
```

<210> SEQ ID NO 13
<211> LENGTH: 2497
<212> TYPE: DNA
<213> ORGANISM: Homo sapiens
<220> FEATURE:
<221> NAME/KEY: CDS
<222> LOCATION: (45)..(2069)

<400> SEQUENCE: 13

```
gggcgccgag gctccccgcc gctcgctgct ccccggcccg cgcc atg ccc tcc tac         56
                                               Met Pro Ser Tyr
                                                 1 acg gtc acc gtg gcc act ggc agc cag tgg ttc gcc ggc act gac gac         104
Thr Val Thr Val Ala Thr Gly Ser Gln Trp Phe Ala Gly Thr Asp Asp
 5                  10                  15                  20 tac atc tac ctc agc ctc gtg ggc tcg gcg ggc tgc agc gag aag cac         152
Tyr Ile Tyr Leu Ser Leu Val Gly Ser Ala Gly Cys Ser Glu Lys His
                 25                  30                  35 ctg ctg gac aag ccc ttc tac aac gac ttc gag cgt ggc gcg gtg gat         200
Leu Leu Asp Lys Pro Phe Tyr Asn Asp Phe Glu Arg Gly Ala Val Asp
             40                  45                  50 tca tac gac gtg act gtg gac gag gaa ctg ggc gag atc cag ctg gtc         248
Ser Tyr Asp Val Thr Val Asp Glu Glu Leu Gly Glu Ile Gln Leu Val
         55                  60                  65 aga atc gag aag cgc aag tac tgg ctg aat gac gac tgg tac ctg aag         296
Arg Ile Glu Lys Arg Lys Tyr Trp Leu Asn Asp Asp Trp Tyr Leu Lys
     70                  75                  80 tac atc acg ctg aag acg ccc cac ggg gac tac atc gag ttc ccc tgc         344
Tyr Ile Thr Leu Lys Thr Pro His Gly Asp Tyr Ile Glu Phe Pro Cys
 85                  90                  95                 100 tac cgc tgg atc acc ggc gat gtc gag gtt gtc ctg agg gat gga cgc         392
Tyr Arg Trp Ile Thr Gly Asp Val Glu Val Val Leu Arg Asp Gly Arg
```

-continued

|  |  |  | 105 |  |  |  | 110 |  |  |  | 115 |  |  |  |
|---|---|---|---|---|---|---|---|---|---|---|---|---|---|---|
| gca | aag | ttg | gcc | cga | gat | gac | caa | att | cac | att | ctc | aag | caa | cac | cga | 440 |
| Ala | Lys | Leu | Ala | Arg | Asp | Asp | Gln | Ile | His | Ile | Leu | Lys | Gln | His | Arg |
|  |  |  | 120 |  |  |  | 125 |  |  |  | 130 |  |  |  |

```
gca aag ttg gcc cga gat gac caa att cac att ctc aag caa cac cga     440
Ala Lys Leu Ala Arg Asp Asp Gln Ile His Ile Leu Lys Gln His Arg
            120                 125                 130 cgt aaa gaa ctg gaa aca cgg caa aaa caa tat cga tgg atg gag tgg     488
Arg Lys Glu Leu Glu Thr Arg Gln Lys Gln Tyr Arg Trp Met Glu Trp
            135                 140                 145 aac cct ggc ttc ccc ttg agc atc gat gcc aaa tgc cac aag gat tta     536
Asn Pro Gly Phe Pro Leu Ser Ile Asp Ala Lys Cys His Lys Asp Leu
        150                 155                 160 ccc cgt gat atc cag ttt gat agt gaa aaa gga gtg gac ttt gtt ctg     584
Pro Arg Asp Ile Gln Phe Asp Ser Glu Lys Gly Val Asp Phe Val Leu
165                 170                 175                 180 aat tac tcc aaa gcg atg gag aac ctg ttc atc aac cgc ttc atg cac     632
Asn Tyr Ser Lys Ala Met Glu Asn Leu Phe Ile Asn Arg Phe Met His
                185                 190                 195 atg ttc cag tct tct tgg aat gac ttc gcc gac ttt gag aaa atc ttt     680
Met Phe Gln Ser Ser Trp Asn Asp Phe Ala Asp Phe Glu Lys Ile Phe
                200                 205                 210 gtc aag atc agc aac act att tct gag cgg gtc atg aat cac tgg cag     728
Val Lys Ile Ser Asn Thr Ile Ser Glu Arg Val Met Asn His Trp Gln
                215                 220                 225 gaa gac ctg atg ttt ggc tac cag ttc ctg aat ggc tgc aac cct gtg     776
Glu Asp Leu Met Phe Gly Tyr Gln Phe Leu Asn Gly Cys Asn Pro Val
230                 235                 240 ttg atc cgg cgc tgc aca gag ctg ccc gag aag ctc ccg gtg acc acg     824
Leu Ile Arg Arg Cys Thr Glu Leu Pro Glu Lys Leu Pro Val Thr Thr
245                 250                 255                 260 gag atg gta gag tgc agc ctg gag cgg cag ctc agc ttg gag cag gag     872
Glu Met Val Glu Cys Ser Leu Glu Arg Gln Leu Ser Leu Glu Gln Glu
                265                 270                 275 gtc cag caa ggg aac att ttc atc gtg gac ttt gag ctg ctg gat ggc     920
Val Gln Gln Gly Asn Ile Phe Ile Val Asp Phe Glu Leu Leu Asp Gly
                280                 285                 290 atc gat gcc aac aaa aca gac ccc tgc aca ctc cag ttc ctg gcc gct     968
Ile Asp Ala Asn Lys Thr Asp Pro Cys Thr Leu Gln Phe Leu Ala Ala
                295                 300                 305 ccc atc tgc ttg ctg tat aag aac ctg gcc aac aag att gtc ccc att    1016
Pro Ile Cys Leu Leu Tyr Lys Asn Leu Ala Asn Lys Ile Val Pro Ile
310                 315                 320 gcc atc cag ctc aac caa atc ccg gga gat gag aac cct att ttc ctc    1064
Ala Ile Gln Leu Asn Gln Ile Pro Gly Asp Glu Asn Pro Ile Phe Leu
325                 330                 335                 340 cct tcg gat gca aaa tac gac tgg ctt ttg gcc aaa atc tgg gtg cgt    1112
Pro Ser Asp Ala Lys Tyr Asp Trp Leu Leu Ala Lys Ile Trp Val Arg
                345                 350                 355 tcc agt gac ttc cac gtc cac cag acc atc acc cac ctt ctg cga aca    1160
Ser Ser Asp Phe His Val His Gln Thr Ile Thr His Leu Leu Arg Thr
                360                 365                 370 cat ctg gtg tct gag gtt ttt ggc att gca atg tac cgc cag ctg cct    1208
His Leu Val Ser Glu Val Phe Gly Ile Ala Met Tyr Arg Gln Leu Pro
                375                 380                 385 gct gtg cac ccc att ttc aag ctg ctg gtg gca cac gtg aga ttc acc    1256
Ala Val His Pro Ile Phe Lys Leu Leu Val Ala His Val Arg Phe Thr
        390                 395                 400 att gca atc aac acc aag gcc cgt gag cag ctc atc tgc gag tgt ggc    1304
Ile Ala Ile Asn Thr Lys Ala Arg Glu Gln Leu Ile Cys Glu Cys Gly
405                 410                 415                 420 ctc ttt gac aag gcc aac gcc aca ggg ggc ggt ggg cac gtg cag atg    1352
```

-continued

```
Leu Phe Asp Lys Ala Asn Ala Thr Gly Gly Gly His Val Gln Met
            425                 430                 435 gtg cag agg gcc atg aag gac ctg acc tat gcc tcc ctg tgc ttt ccc    1400
Val Gln Arg Ala Met Lys Asp Leu Thr Tyr Ala Ser Leu Cys Phe Pro
                440                 445                 450 gag gcc atc aag gcc cgg ggc atg gag agc aaa gaa gac atc ccc tac    1448
Glu Ala Ile Lys Ala Arg Gly Met Glu Ser Lys Glu Asp Ile Pro Tyr
            455                 460                 465 tac ttc tac cgg gac gac ggg ctc ctg gtg tgg gaa gcc atc agg acg    1496
Tyr Phe Tyr Arg Asp Asp Gly Leu Leu Val Trp Glu Ala Ile Arg Thr
        470                 475                 480 ttc acg gcc gag gtg gta gac atc tac tac gag ggc gac cag gtg gtg    1544
Phe Thr Ala Glu Val Val Asp Ile Tyr Tyr Glu Gly Asp Gln Val Val
485                 490                 495                 500 gag gag gac ccg gag ctg cag gac ttc gtg aac gat gtc tac gtg tac    1592
Glu Glu Asp Pro Glu Leu Gln Asp Phe Val Asn Asp Val Tyr Val Tyr
                505                 510                 515 ggc atg cgg ggc cgc aag tcc tca ggc ttc ccc aag tcg gtc aag agc    1640
Gly Met Arg Gly Arg Lys Ser Ser Gly Phe Pro Lys Ser Val Lys Ser
            520                 525                 530 cgg gag cag ctg tcg gag tac ctg acc gtg gtg atc ttc acc gcc tcc    1688
Arg Glu Gln Leu Ser Glu Tyr Leu Thr Val Val Ile Phe Thr Ala Ser
        535                 540                 545 gcc cag cac gcc gcg gtc aac ttc ggc cag tac gac tgg tgc tcc tgg    1736
Ala Gln His Ala Ala Val Asn Phe Gly Gln Tyr Asp Trp Cys Ser Trp
    550                 555                 560 atc ccc aat gcg ccc cca acc atg cga gcc ccg cca ccg act gcc aag    1784
Ile Pro Asn Ala Pro Pro Thr Met Arg Ala Pro Pro Pro Thr Ala Lys
565                 570                 575                 580 ggc gtg gtg acc att gag cag atc gtg gac acg ctg ccc gac cgc ggc    1832
Gly Val Val Thr Ile Glu Gln Ile Val Asp Thr Leu Pro Asp Arg Gly
                585                 590                 595 cgc tcc tgc tgg cat ctg ggt gca gtg tgg gcg ctg agc cag ttc cag    1880
Arg Ser Cys Trp His Leu Gly Ala Val Trp Ala Leu Ser Gln Phe Gln
            600                 605                 610 gaa aac gag ctg ttc ctg ggc atg tac cca gaa gag cat ttt atc gag    1928
Glu Asn Glu Leu Phe Leu Gly Met Tyr Pro Glu Glu His Phe Ile Glu
        615                 620                 625 aag cct gtg aag gaa gcc atg gcc cga ttc cgc aag aac ctc gag gcc    1976
Lys Pro Val Lys Glu Ala Met Ala Arg Phe Arg Lys Asn Leu Glu Ala
    630                 635                 640 att gtc agc gtg att gct gag cgc aac aag aag cag ctg cca tat        2024
Ile Val Ser Val Ile Ala Glu Arg Asn Lys Lys Gln Leu Pro Tyr
645                 650                 655                 660 tac tac ttg tcc cca gac cgg att ccg aac agt gtg gcc atc tga        2069
Tyr Tyr Leu Ser Pro Asp Arg Ile Pro Asn Ser Val Ala Ile
                665                 670 gcacactgcc agtctcactg tgggaaggcc agctgcccca gccagatgga ctccagcctg    2129
cctggcaggc tgtctggcca ggcctcttgg cagtcacatc tcttcctccg aggccagtac    2189
ctttccattt attctttgat cttcagggaa ctgcatagat tgtatcaaag tgtaaacacc    2249 ataggggaccc attctacaca gagcaggact gcacaggcgt cctgtccaca cccagctcag    2309
catttccaca ccaagcagca acagcaaatc acgaccactg atagatgtct attcttgttg    2369
gagacatggg atgattattt tctgttctat ttgtgcttag tccaattcct tgcacatagt    2429
aggtacccaa ttcaattact attgaatgaa ttaagaattg gttgccataa aaataaatca    2489
gttcattt                                                              2497
```

<210> SEQ ID NO 14
<211> LENGTH: 674
<212> TYPE: PRT
<213> ORGANISM: Homo sapiens

<400> SEQUENCE: 14

```
Met Pro Ser Tyr Thr Val Thr Val Ala Thr Gly Ser Gln Trp Phe Ala
1               5                   10                  15

Gly Thr Asp Asp Tyr Ile Tyr Leu Ser Leu Val Gly Ser Ala Gly Cys
            20                  25                  30

Ser Glu Lys His Leu Leu Asp Lys Pro Phe Tyr Asn Asp Phe Glu Arg
        35                  40                  45

Gly Ala Val Asp Ser Tyr Asp Val Thr Val Asp Glu Glu Leu Gly Glu
    50                  55                  60

Ile Gln Leu Val Arg Ile Glu Lys Arg Lys Tyr Trp Leu Asn Asp Asp
65                  70                  75                  80

Trp Tyr Leu Lys Tyr Ile Thr Leu Lys Thr Pro His Gly Asp Tyr Ile
                85                  90                  95

Glu Phe Pro Cys Tyr Arg Trp Ile Thr Gly Asp Val Glu Val Val Leu
            100                 105                 110

Arg Asp Gly Arg Ala Lys Leu Ala Arg Asp Asp Gln Ile His Ile Leu
        115                 120                 125

Lys Gln His Arg Arg Lys Glu Leu Glu Thr Arg Gln Lys Gln Tyr Arg
    130                 135                 140

Trp Met Glu Trp Asn Pro Gly Phe Pro Leu Ser Ile Asp Ala Lys Cys
145                 150                 155                 160

His Lys Asp Leu Pro Arg Asp Ile Gln Phe Asp Ser Glu Lys Gly Val
                165                 170                 175

Asp Phe Val Leu Asn Tyr Ser Lys Ala Met Glu Asn Leu Phe Ile Asn
            180                 185                 190

Arg Phe Met His Met Phe Gln Ser Ser Trp Asn Asp Phe Ala Asp Phe
        195                 200                 205

Glu Lys Ile Phe Val Lys Ile Ser Asn Thr Ile Ser Glu Arg Val Met
    210                 215                 220

Asn His Trp Gln Glu Asp Leu Met Phe Gly Tyr Gln Phe Leu Asn Gly
225                 230                 235                 240

Cys Asn Pro Val Leu Ile Arg Arg Cys Thr Glu Leu Pro Glu Lys Leu
                245                 250                 255

Pro Val Thr Thr Glu Met Val Glu Cys Ser Leu Glu Arg Gln Leu Ser
            260                 265                 270

Leu Glu Gln Glu Val Gln Gln Gly Asn Ile Phe Ile Val Asp Phe Glu
        275                 280                 285

Leu Leu Asp Gly Ile Asp Ala Asn Lys Thr Asp Pro Cys Thr Leu Gln
    290                 295                 300

Phe Leu Ala Ala Pro Ile Cys Leu Leu Tyr Lys Asn Leu Ala Asn Lys
305                 310                 315                 320

Ile Val Pro Ile Ala Ile Gln Leu Asn Gln Ile Pro Gly Asp Glu Asn
                325                 330                 335

Pro Ile Phe Leu Pro Ser Asp Ala Lys Tyr Asp Trp Leu Leu Ala Lys
            340                 345                 350

Ile Trp Val Arg Ser Ser Asp Phe His Val His Gln Thr Ile Thr His
        355                 360                 365

Leu Leu Arg Thr His Leu Val Ser Glu Val Phe Gly Ile Ala Met Tyr
    370                 375                 380
```

```
Arg Gln Leu Pro Ala Val His Pro Ile Phe Lys Leu Val Ala His
385                 390                 395                 400

Val Arg Phe Thr Ile Ala Ile Asn Thr Lys Ala Arg Glu Gln Leu Ile
                405                 410                 415

Cys Glu Cys Gly Leu Phe Asp Lys Ala Asn Ala Thr Gly Gly Gly Gly
                420                 425                 430

His Val Gln Met Val Gln Arg Ala Met Lys Asp Leu Thr Tyr Ala Ser
                435                 440                 445

Leu Cys Phe Pro Glu Ala Ile Lys Ala Arg Gly Met Glu Ser Lys Glu
    450                 455                 460

Asp Ile Pro Tyr Tyr Phe Tyr Arg Asp Asp Gly Leu Leu Val Trp Glu
465                 470                 475                 480

Ala Ile Arg Thr Phe Thr Ala Glu Val Val Asp Ile Tyr Tyr Glu Gly
                485                 490                 495

Asp Gln Val Val Glu Glu Asp Pro Glu Leu Gln Asp Phe Val Asn Asp
                500                 505                 510

Val Tyr Val Tyr Gly Met Arg Gly Arg Lys Ser Ser Gly Phe Pro Lys
                515                 520                 525

Ser Val Lys Ser Arg Glu Gln Leu Ser Glu Tyr Leu Thr Val Val Ile
    530                 535                 540

Phe Thr Ala Ser Ala Gln His Ala Ala Val Asn Phe Gly Gln Tyr Asp
545                 550                 555                 560

Trp Cys Ser Trp Ile Pro Asn Ala Pro Pro Thr Met Arg Ala Pro Pro
                565                 570                 575

Pro Thr Ala Lys Gly Val Val Thr Ile Glu Gln Ile Val Asp Thr Leu
                580                 585                 590

Pro Asp Arg Gly Arg Ser Cys Trp His Leu Gly Ala Val Trp Ala Leu
                595                 600                 605

Ser Gln Phe Gln Glu Asn Glu Leu Phe Leu Gly Met Tyr Pro Glu Glu
    610                 615                 620

His Phe Ile Glu Lys Pro Val Lys Glu Ala Met Ala Arg Phe Arg Lys
625                 630                 635                 640

Asn Leu Glu Ala Ile Val Ser Val Ile Ala Glu Arg Asn Lys Lys Lys
                645                 650                 655

Gln Leu Pro Tyr Tyr Tyr Leu Ser Pro Asp Arg Ile Pro Asn Ser Val
                660                 665                 670

Ala Ile

<210> SEQ ID NO 15
<211> LENGTH: 2420
<212> TYPE: DNA
<213> ORGANISM: Homo sapiens
<220> FEATURE:
<221> NAME/KEY: CDS
<222> LOCATION: (3)..(1994)

<400> SEQUENCE: 15 ct tca ccc cgt ggt gaa gac act gac gac tac atc tac ctc agc ctc      47
   Ser Pro Arg Gly Glu Asp Thr Asp Asp Tyr Ile Tyr Leu Ser Leu
   1               5                   10                  15 gtg ggc tcg gcg ggc tgc agc gag aag cac ctg ctg gac aag ccc ttc     95
Val Gly Ser Ala Gly Cys Ser Glu Lys His Leu Leu Asp Lys Pro Phe
                20                  25                  30 tac aac gac ttc gag cgt ggc gcg gtg gat tca tac gac gtg act gtg    143
Tyr Asn Asp Phe Glu Arg Gly Ala Val Asp Ser Tyr Asp Val Thr Val
            35                  40                  45
```

```
                                                               -continued gac gag gaa ctg ggc gag atc cag ctg gtc aga atc gag aag cgc aag        191
Asp Glu Glu Leu Gly Glu Ile Gln Leu Val Arg Ile Glu Lys Arg Lys
         50                  55                  60 tac tgg ctg aat gac gac tgg tac ctg aag tac atc acg ctg aag acg        239
Tyr Trp Leu Asn Asp Asp Trp Tyr Leu Lys Tyr Ile Thr Leu Lys Thr
 65                  70                  75 ccc cac ggg gac tac atc gag ttc ccc tgc tac cgc tgg atc acc ggc        287
Pro His Gly Asp Tyr Ile Glu Phe Pro Cys Tyr Arg Trp Ile Thr Gly
 80                  85                  90                  95 gat gtc gag gtt gtc ctg agg gat gga cgc gca aag ttg gcc cga gat        335
Asp Val Glu Val Val Leu Arg Asp Gly Arg Ala Lys Leu Ala Arg Asp
                100                 105                 110 gac caa att cac att ctc aag caa cac cga cgt aaa gaa ctg gaa aca        383
Asp Gln Ile His Ile Leu Lys Gln His Arg Arg Lys Glu Leu Glu Thr
            115                 120                 125 cgg caa aaa caa tat cga tgg atg gag tgg aac cct ggc ttc ccc ttg        431
Arg Gln Lys Gln Tyr Arg Trp Met Glu Trp Asn Pro Gly Phe Pro Leu
        130                 135                 140 agc atc gat gcc aaa tgc cac aag gat tta ccc cgt gat atc cag ttt        479
Ser Ile Asp Ala Lys Cys His Lys Asp Leu Pro Arg Asp Ile Gln Phe
145                 150                 155 gat agt gaa aaa gga gtg gac ttt gtt ctg aat tac tcc aaa gcg atg        527
Asp Ser Glu Lys Gly Val Asp Phe Val Leu Asn Tyr Ser Lys Ala Met
160                 165                 170                 175 gag aac ctg ttc atc aac cgc ttc atg cac atg ttc cag tct tct tgg        575
Glu Asn Leu Phe Ile Asn Arg Phe Met His Met Phe Gln Ser Ser Trp
                180                 185                 190 aat gac ttc gcc gac ttt gag aaa atc ttt gtc aag atc agc aac act        623
Asn Asp Phe Ala Asp Phe Glu Lys Ile Phe Val Lys Ile Ser Asn Thr
            195                 200                 205 att tct gag cgg gtc atg aat cac tgg cag gaa gac ctg atg ttt ggc        671
Ile Ser Glu Arg Val Met Asn His Trp Gln Glu Asp Leu Met Phe Gly
        210                 215                 220 tac cag ttc ctg aat ggc tgc aac cct gtg ttg atc cgg cgc tgc aca        719
Tyr Gln Phe Leu Asn Gly Cys Asn Pro Val Leu Ile Arg Arg Cys Thr
    225                 230                 235 gag ctg ccc gag aag ctc ccg gtg acc acg gag atg gta gag tgc agc        767
Glu Leu Pro Glu Lys Leu Pro Val Thr Thr Glu Met Val Glu Cys Ser
240                 245                 250                 255 ctg gag cgg cag ctc agc ttg gag cag gag gtc cag caa ggg aac att        815
Leu Glu Arg Gln Leu Ser Leu Glu Gln Glu Val Gln Gln Gly Asn Ile
                260                 265                 270 ttc atc gtg gac ttt gag ctg ctg gat ggc atc gat gcc aac aaa aca        863
Phe Ile Val Asp Phe Glu Leu Leu Asp Gly Ile Asp Ala Asn Lys Thr
            275                 280                 285 gac ccc tgc aca ctc cag ttc ctg gcc gct ccc atc tgc ttg ctg tat        911
Asp Pro Cys Thr Leu Gln Phe Leu Ala Ala Pro Ile Cys Leu Leu Tyr
        290                 295                 300 aag aac ctg gcc aac aag att gtc ccc att gcc atc cag ctc aac caa        959
Lys Asn Leu Ala Asn Lys Ile Val Pro Ile Ala Ile Gln Leu Asn Gln
    305                 310                 315 atc ccg gga gat gag aac cct att ttc ctc cct tcg gat gca aaa tac       1007
Ile Pro Gly Asp Glu Asn Pro Ile Phe Leu Pro Ser Asp Ala Lys Tyr
320                 325                 330                 335 gac tgg ctt ttg gcc aaa atc tgg gtg cgt tcc agt gac ttc cac gtc       1055
Asp Trp Leu Leu Ala Lys Ile Trp Val Arg Ser Ser Asp Phe His Val
                340                 345                 350 cac cag acc atc acc cac ctt ctg cga aca cat ctg gtg tct gag gtt       1103
His Gln Thr Ile Thr His Leu Leu Arg Thr His Leu Val Ser Glu Val
```

-continued

```
                   355                 360                 365
ttt ggc att gca atg tac cgc cag ctg cct gct gtg cac ccc att ttc    1151
Phe Gly Ile Ala Met Tyr Arg Gln Leu Pro Ala Val His Pro Ile Phe
        370                 375                 380 aag ctg ctg gtg gca cac gtg aga ttc acc att gca atc aac acc aag    1199
Lys Leu Leu Val Ala His Val Arg Phe Thr Ile Ala Ile Asn Thr Lys
    385                 390                 395 gcc cgt gag cag ctc atc tgc gag tgt ggc ctc ttt gac aag gcc aac    1247
Ala Arg Glu Gln Leu Ile Cys Glu Cys Gly Leu Phe Asp Lys Ala Asn
400                 405                 410                 415 gcc aca ggg ggc ggt ggg cac gtg cag atg gtg cag agg gcc atg aag    1295
Ala Thr Gly Gly Gly Gly His Val Gln Met Val Gln Arg Ala Met Lys
                420                 425                 430 gac ctg acc tat gcc tcc ctg tgc ttt ccc gag gcc atc aag gcc cgg    1343
Asp Leu Thr Tyr Ala Ser Leu Cys Phe Pro Glu Ala Ile Lys Ala Arg
            435                 440                 445 ggc atg gag agc aaa gaa gac atc ccc tac tac ttc tac cgg gac gac    1391
Gly Met Glu Ser Lys Glu Asp Ile Pro Tyr Tyr Phe Tyr Arg Asp Asp
        450                 455                 460 ggg ctc ctg gtg tgg gaa gcc atc agg acg ttc acg gcc gag gtg gta    1439
Gly Leu Leu Val Trp Glu Ala Ile Arg Thr Phe Thr Ala Glu Val Val
    465                 470                 475 gac atc tac tac gag ggc gac cag gtg gtg gag gag gac ccg gag ctg    1487
Asp Ile Tyr Tyr Glu Gly Asp Gln Val Val Glu Glu Asp Pro Glu Leu
480                 485                 490                 495 cag gac ttc gtg aac gat gtc tac gtg tac ggc atg cgg ggc cgc aag    1535
Gln Asp Phe Val Asn Asp Val Tyr Val Tyr Gly Met Arg Gly Arg Lys
                500                 505                 510 tcc tca ggc ttc ccc aag tcg gtc aag agc cgg gag cag ctg tcg gag    1583
Ser Ser Gly Phe Pro Lys Ser Val Lys Ser Arg Glu Gln Leu Ser Glu
            515                 520                 525 tac ctg acc gtg gtg atc ttc acc gcc tcc gcc cag cac gcc gcg gtc    1631
Tyr Leu Thr Val Val Ile Phe Thr Ala Ser Ala Gln His Ala Ala Val
        530                 535                 540 aac ttc ggc cag tac gac tgg tgc tcc tgg atc ccc aat gcg ccc cca    1679
Asn Phe Gly Gln Tyr Asp Trp Cys Ser Trp Ile Pro Asn Ala Pro Pro
    545                 550                 555 acc atg cga gcc ccg cca ccg act gcc aag ggc gtg gtg acc att gag    1727
Thr Met Arg Ala Pro Pro Pro Thr Ala Lys Gly Val Val Thr Ile Glu
560                 565                 570                 575 cag atc gtg gac acg ctg ccc gac cgc ggc cgc tcc tgc tgg cat ctg    1775
Gln Ile Val Asp Thr Leu Pro Asp Arg Gly Arg Ser Cys Trp His Leu
                580                 585                 590 ggt gca gtg tgg gcg ctg agc cag ttc cag gaa aac gag ctg ttc ctg    1823
Gly Ala Val Trp Ala Leu Ser Gln Phe Gln Glu Asn Glu Leu Phe Leu
            595                 600                 605 ggc atg tac cca gaa gag cat ttt atc gag aag cct gtg aag gaa gcc    1871
Gly Met Tyr Pro Glu Glu His Phe Ile Glu Lys Pro Val Lys Glu Ala
        610                 615                 620 atg gcc cga ttc cgc aag aac ctc gag gcc att gtc agc gtg att gct    1919
Met Ala Arg Phe Arg Lys Asn Leu Glu Ala Ile Val Ser Val Ile Ala
    625                 630                 635 gag cgc aac aag aag aag cag ctg cca tat tac tac ttg tcc cca gac    1967
Glu Arg Asn Lys Lys Lys Gln Leu Pro Tyr Tyr Tyr Leu Ser Pro Asp
640                 645                 650                 655 cgg att ccg aac agt gtg gcc atc tga gcacactgcc agtctcactg           2014
Arg Ile Pro Asn Ser Val Ala Ile
                660 tgggaaggcc agctgccccca gccagatgga ctccagcctg cctggcaggc tgtctggcca   2074
```

-continued

```
ggcctcttgg cagtcacatc tcttcctccg aggccagtac ctttccattt attctttgat      2134
cttcagggaa ctgcatagat tgatcaaagt gtaaacacca tagggaccca ttctacacag      2194
agcaggactg cacagcgtcc tgtccacacc cagctcagca tttccacacc aagcagcaac      2254
agcaaatcac gaccactgat agatgtctat tcttgttgga gacatgggat gattattttc      2314
tgttctattt gtgcttagtc caattccttg cacatagtag gtacccaatt caattactat      2374
tgaatgaatt aagaattggt tgccataaaa ataaatcagt tcattt                     2420
```

<210> SEQ ID NO 16
<211> LENGTH: 663
<212> TYPE: PRT
<213> ORGANISM: Homo sapiens

<400> SEQUENCE: 16

```
Ser Pro Arg Gly Glu Asp Thr Asp Asp Tyr Ile Tyr Leu Ser Leu Val
1               5                  10                   15

Gly Ser Ala Gly Cys Ser Glu Lys His Leu Leu Asp Lys Pro Phe Tyr
            20                  25                  30

Asn Asp Phe Glu Arg Gly Ala Val Asp Ser Tyr Asp Val Thr Val Asp
        35                  40                  45

Glu Glu Leu Gly Glu Ile Gln Leu Val Arg Ile Glu Lys Arg Lys Tyr
    50                  55                  60

Trp Leu Asn Asp Asp Trp Tyr Leu Lys Tyr Ile Thr Leu Lys Thr Pro
65                  70                  75                  80

His Gly Asp Tyr Ile Glu Phe Pro Cys Tyr Arg Trp Ile Thr Gly Asp
                85                  90                  95

Val Glu Val Val Leu Arg Asp Gly Arg Ala Lys Leu Ala Arg Asp Asp
            100                 105                 110

Gln Ile His Ile Leu Lys Gln His Arg Arg Lys Glu Leu Glu Thr Arg
        115                 120                 125

Gln Lys Gln Tyr Arg Trp Met Glu Trp Asn Pro Gly Phe Pro Leu Ser
    130                 135                 140

Ile Asp Ala Lys Cys His Lys Asp Leu Pro Arg Asp Ile Gln Phe Asp
145                 150                 155                 160

Ser Glu Lys Gly Val Asp Phe Val Leu Asn Tyr Ser Lys Ala Met Glu
                165                 170                 175

Asn Leu Phe Ile Asn Arg Phe Met His Met Phe Gln Ser Ser Trp Asn
            180                 185                 190

Asp Phe Ala Asp Phe Glu Lys Ile Phe Val Lys Ile Ser Asn Thr Ile
        195                 200                 205

Ser Glu Arg Val Met Asn His Trp Gln Glu Asp Leu Met Phe Gly Tyr
    210                 215                 220

Gln Phe Leu Asn Gly Cys Asn Pro Val Leu Ile Arg Arg Cys Thr Glu
225                 230                 235                 240

Leu Pro Glu Lys Leu Pro Val Thr Thr Glu Met Val Glu Cys Ser Leu
                245                 250                 255

Glu Arg Gln Leu Ser Leu Glu Gln Val Gln Gly Asn Ile Phe
            260                 265                 270

Ile Val Asp Phe Glu Leu Leu Asp Gly Ile Asp Ala Asn Lys Thr Asp
        275                 280                 285

Pro Cys Thr Leu Gln Phe Leu Ala Ala Pro Ile Cys Leu Leu Tyr Lys
    290                 295                 300

Asn Leu Ala Asn Lys Ile Val Pro Ile Ala Ile Gln Leu Asn Gln Ile
```

-continued

```
305                 310                 315                 320

Pro Gly Asp Glu Asn Pro Ile Phe Leu Pro Ser Asp Ala Lys Tyr Asp
                325                 330                 335

Trp Leu Leu Ala Lys Ile Trp Val Arg Ser Ser Asp Phe His Val His
                340                 345                 350

Gln Thr Ile Thr His Leu Leu Arg Thr His Leu Val Ser Glu Val Phe
                355                 360                 365

Gly Ile Ala Met Tyr Arg Gln Leu Pro Ala Val His Pro Ile Phe Lys
        370                 375                 380

Leu Leu Val Ala His Val Arg Phe Thr Ile Ala Ile Asn Thr Lys Ala
385                 390                 395                 400

Arg Glu Gln Leu Ile Cys Glu Cys Gly Leu Phe Asp Lys Ala Asn Ala
                405                 410                 415

Thr Gly Gly Gly His Val Gln Met Val Gln Arg Ala Met Lys Asp
                420                 425                 430

Leu Thr Tyr Ala Ser Leu Cys Phe Pro Glu Ala Ile Lys Ala Arg Gly
        435                 440                 445

Met Glu Ser Lys Glu Asp Ile Pro Tyr Tyr Phe Tyr Arg Asp Asp Gly
    450                 455                 460

Leu Leu Val Trp Glu Ala Ile Arg Thr Phe Thr Ala Glu Val Val Asp
465                 470                 475                 480

Ile Tyr Tyr Glu Gly Asp Gln Val Val Glu Glu Asp Pro Glu Leu Gln
                485                 490                 495

Asp Phe Val Asn Asp Val Tyr Val Tyr Gly Met Arg Gly Arg Lys Ser
                500                 505                 510

Ser Gly Phe Pro Lys Ser Val Lys Ser Arg Glu Gln Leu Ser Glu Tyr
        515                 520                 525

Leu Thr Val Val Ile Phe Thr Ala Ser Ala Gln His Ala Ala Val Asn
    530                 535                 540

Phe Gly Gln Tyr Asp Trp Cys Ser Trp Ile Pro Asn Ala Pro Pro Thr
545                 550                 555                 560

Met Arg Ala Pro Pro Thr Ala Lys Gly Val Val Thr Ile Glu Gln
                565                 570                 575

Ile Val Asp Thr Leu Pro Asp Arg Gly Arg Ser Cys Trp His Leu Gly
                580                 585                 590

Ala Val Trp Ala Leu Ser Gln Phe Gln Glu Asn Glu Leu Phe Leu Gly
        595                 600                 605

Met Tyr Pro Glu Glu His Phe Ile Glu Lys Pro Val Lys Glu Ala Met
    610                 615                 620

Ala Arg Phe Arg Lys Asn Leu Glu Ala Ile Val Ser Val Ile Ala Glu
625                 630                 635                 640

Arg Asn Lys Lys Lys Gln Leu Pro Tyr Tyr Tyr Leu Ser Pro Asp Arg
                645                 650                 655

Ile Pro Asn Ser Val Ala Ile
                660
```

MEDICINE RESPONSE ASSAY IN RESPIRATORY DISEASE

This application is filed pursuant to 35 U.S.C. § 371 as a United States National Phase Application of International Application No. PCT/US01/12534 filed Apr. 17, 2001, which claims priority from U.S. Provisional Application No. 60/197,913 filed Apr. 17, 2000, and U.S. Provisional Application No. 60/236,608 filed Sep. 29, 2000.

FIELD OF THE INVENTION

The present studies relate to polymorphisms in genes that play a role in the biosynthesis of sulfidopeptide leukotrienes, and phenotypes that are associated or correlated therewith. More particularly, the present studies relate to the correlation of such polymorphisms to the response of subjects with respiratory disorders (such as asthma) to pharmaceutical treatment. The present studies further relate to methods of screening compounds for pharmaceutical activity. The present studies also relate to methods of genotyping subjects for predictive purposes.

BACKGROUND OF THE INVENTION

Asthma is an extremely common disorder accounting for 1 to 3% of all office visits, 500,000 hospital admissions per year and more pediatric hospital admissions than any other single illness. Asthma is no longer simply viewed as reversible airway obstruction or irritable airways. Rather, it is viewed primarily as an inflammatory illness that has bronchial hyperreactivity and bronchospasm as a result. The asthmatic inflammation that underlies the disease can be addressed by therapy with anti-inflammatory agents such as glucocorticoids or by those agents that target the role of the leukotrienes in the inflammation process.

The leukotrienes are a family of eicosatetraenoic acids derived from arachidonic acid which exhibit a wide range of pharmacological and physiological activities including bronchoconstriction and proinflammatory activity. Arachidonic acid is cleaved from the cell membrane, and acted upon by a cascade of enzymes localized to the perinuclear membrane including 5-lipoxygenase (ALOX5) which forms an unstable epoxide LTC4, followed by the addition of glutathione by LTC4 Synthase (LTC4S) forming the intercellular LTC4. LTC4 is transported extracellularly, where an amino acid is sequentially cleaved to form cystinyl leukotrienes LTD4 and LTE4. The cystinyl leukotrienes LTD4 and LTE4 act through the CYS-LT1 receptor. Two classes of drugs exist to modulate this pathway, ALOX5 inhibitors and CYSLT1 receptor antagonists.

A polymorphism in the promoter region of the ALOX5 gene has been demonstrated to affect the transcription of this gene. In vitro, human cells containing other than 5 random repeats of the Sp-1 binding motif (GGGCGG) have diminished activity. It follows that patients with asthma that have a variant genotype would be less responsive to therapeutic intervention with agents modifying this pathway. Prior clinical trials with the ALOX5 inhibitor compound ABT-761 have determined that efficacy of the compound is affected by genotype (Drazen, J. M. et al Pharmacogenetic association between ALOX5 promoter genotype and the response to anti-asthma treatment. Nature Genetics 22;168–170, 1999). Patients that were either homozygous for the wild type allele (5 tandem repeats of the Sp-1 motif) or heterozygous (5/any other number of tandem repeats) had similar efficacy. However, the patients that were homozygous for no wild type alleles (variants) had a greatly reduced response to the compound. See FIG. 1 (which graphs data provided in Drazen et al. (1999) at page 168, column 2, last paragraph, continuing to page 169). In FIG. 1, homozygous for the wild type allele is denoted 5,5; heterozygous the wild and variant alleles is denoted 5,X; and homozygous for variant alleles is denoted X,X.

There is a need for a method of determining whether a given asthma patient would or would not be a good candidate for treatment with a leukotriene pathway modulator. It is therefore a goal of the present invention to provide an association between optimum clinical outcome of pharmacologic therapy and the genotype of the individual population. It is another goal of the present invention to be able to stratify patient populations into those subsets that will respond to a given pharmacologic therapy more or less well relative to other pharmacologic therapies. Another goal of the present invention is to be able to predict a patient's response to a given pharmacologic therapy on the basis of that patient's genotype. An additional goal of the present invention is to provide for a commercial method of predicting patient responses to pharmacologic therapies. Yet another goal of the present invention is to provide a method of screening candidate drug compounds for future suitable administration to a patient or to a patient population, based upon the genotype of the patient or the population. This entails a method of screening candidate drug compounds for variations in a measurable phenotypic effect among genetic subpopulations of subjects with asthma.

SUMMARY OF THE INVENTION

The present inventors have determined that in subjects with respiratory disorders that are potentially treatable with leukotriene receptor antagonists, polymorphisms in the 5-lipoxygenase (ALOX5) gene and/or the leukotriene $C_4$ synthase gene (LTC4S) are correlated with the response of the subjects to pharmacologic therapy with a leukotriene receptor antagonist. More particularly, they have found that a transversion polymorphism in the promoter region of the LTC4S gene is a predictor for the response of patients with asthma to treatment with a CysLT1 leukotriene receptor antagonist, and they have found that a polymorphic variation in the number of tandem repeats of a Sp-1 binding motif in the promoter region of the ALOX5 gene, as well as other transversion polymorphisms, likewise are predictors for the response of patients with asthma to treatment with a CysLT1 leukotriene receptor antagonist; and furthermore, they have identified a genetic subset of asthma patients who display a lower incidence of relief of asthma symptoms when treated with a leukotriene receptor antagonist as compared to alternative pharmacologic therapies.

A first aspect of the present invention is a method of screening a patient population to identify those subjects with an decreased likelihood of responding favorably to treatment with a leukotriene antagonist for a respiratory disease such as asthma. The subjects may have been previously diagnosed with the respiratory disease, or the screening may be used in conjunction with diagnostic efforts.

A further aspect of the present invention is a method of screening a subject with a respiratory disease that is treatable with leukotriene receptor antagonists (such as asthma), as an aid in predicting the subject's response to treatment with a leukotriene receptor antagonist. The method comprises obtaining a sample of the subject's DNA and determining the genotype of the subject at a polymorphic allelic site in either one or both of the ALOX5 gene or the LTC4S gene, where different genotypes at that site have been associated with different incidences of a phenotypic response to treatment with a leukotriene receptor antagonist.

A further aspect of the present invention is a method of screening a subject suffering from asthma that is treatable with a leukotriene receptor antagonist ligand, as an aid in predicting the subject's response to treatment with that leukotriene receptor antagonist. The method comprises obtaining a sample of the subject's DNA and determining the genotype of the subject at a polymorphic allelic site in either or both of the ALOX5 gene and the LTC4S gene, where different genotypes at that site have been associated with different incidences of a phenotypic response to treatment with a leukotriene receptor antagonist. The genotype that is detected in the sample indicates that the subject is likely to have the phenotypic response associated with that genotype.

A further aspect of the present invention is a method of screening a ligand for variations in measurable phenotypic effects among genetic subpopulations of subjects with a respiratory disorder. The method comprises administering the candidate ligand to a population of subjects suffering from the respiratory disorder, and obtaining DNA samples from each of the subjects. The DNA samples are genotyped for a polymorphic allele of the ALOX5 gene and/or the LTC4S gene, and correlations between the polymorphic allele genotype and the occurrence of a phenotypic response in the population of subjects are determined. Detection of a genotype that is correlated with an increased or decreased incidence of a desired therapeutic response or a side effect (compared to the incidence in subjects with alternative genotypes) indicates that the effectiveness of the ligand in treating the respiratory disease varies among genetic subpopulations.

Clinical trials of the type discussed in this application generate various kinds of data that is advantageously stored on electronically readable media, including, but not limited to magnetic tapes, magnetic disks, solid state memory and storage devices, optically readable disks and any combination of these. Such data is also advantageously transmitted or communicated via telecommunications means including metallic or optical fiber lines or via wireless electromagnetic frequency devices. Additionally, such data is advantageously communicated via at least two or more electronic computing devices, including personal computers, computer workstations, computer servers, mainframe computers, super computers and the like. Such communications can occur either directly from device to device or through a plurality of such devices that have been electronically instructed on how to route such communications from a sender to a designated receiver of such communication, including, but not limited to, organizational intranets and the internet or the world wide web. Such data that can be stored and communicated in the above ways include, but are not limited to, any nucleotide sequence data, amino acid sequence data, protein-protein interaction data, clinical diagnosis data or statistics data generated by the above clinical trials. The use of such electronic devices as described is an alternative embodiment of the invention claimed herein, particularly when used commercially.

Additionally, the present invention affords a way of designing and conducting clinical trials in such a way as to take advantage of those patients who do not respond to a leukotriene receptor antagonist, by re-testing that population in a way calculated to increase the likelihood of discovering therapies for such non-responding patients. Presently, the marketing of novel medicines requires extensive clinical trials conducted to demonstrate the efficacy and safety of the candidate medicine. In any given clinical trial, there will be an observed percentage of the patients enrolled in that trial who will either respond to the candidate medicine as hoped for, or who will respond less strongly, or who will not respond at all. Also, there are three possible adverse side effect outcomes, namely no adverse side effect, some acceptable degree of adverse side effect, and an unacceptable adverse side effect. Currently available data suggest that a major part of the partial responders or non-responders populations results from multiple etiologies leading to the recognized phenotype. Single nucleotide polymorphism (SNP) profiling of different medicine-responsive association groups during such clinical studies implies that the location of genes contributing to heterogeneous forms of the disease can also be identified, leading to the discovery of additional susceptibility targets.

A systematic study of those populations of patients who respond to a given medicine is complemented by a study of the converse, that is, a systematic study of those subgroups of patients who did not respond with efficacy and acceptable safety outcomes to the initially studied medicine. Such partial responders or non-responders could be identified in real time, rather than by the current trial and error system that performs this function once a medicine appears in the marketplace. Currently drugs are broadly marketed to many patients who will not benefit and who may experience adverse reactions. Little information of use is obtained from these patients currently, other than broad warnings for use in product labeling.

There is thus a need in the art for a method of designing human clinical drug trials in a fashion that benefits available patient populations through 1) minimizing the likelihood of adverse events, 2) maximizing the likelihood of therapeutic response and 3) providing a pool of data that readily suggests a subsequent clinical trial that is capable of utilizing all prior data, whether for responders or for non-responder. The present invention therefore additionally includes a method of conducting clinical drug trials by pharmacogenetic stratification of a patient population, comprising the steps of conducting a first clinical drug trial on a patient population, such that said drug trial identifies an association between a phenotype (response or non-response to a leukotriene antagonist) and a genotype; separating said patient population in said clinical drug trial into subpopulations of responders and non-responders; conducting a subsequent clinical drug trial on a non-responder patient population such that said subsequent drug trial identifies a subsequent association between a phenotype and a genotype; separating the patient population of step (c) into subsequent responder and subsequent non-responder patient populations; and then repeating steps (c) and (d) through as many iterations as desired.

DETAILED DESCRIPTION OF THE INVENTION

Figure 1:
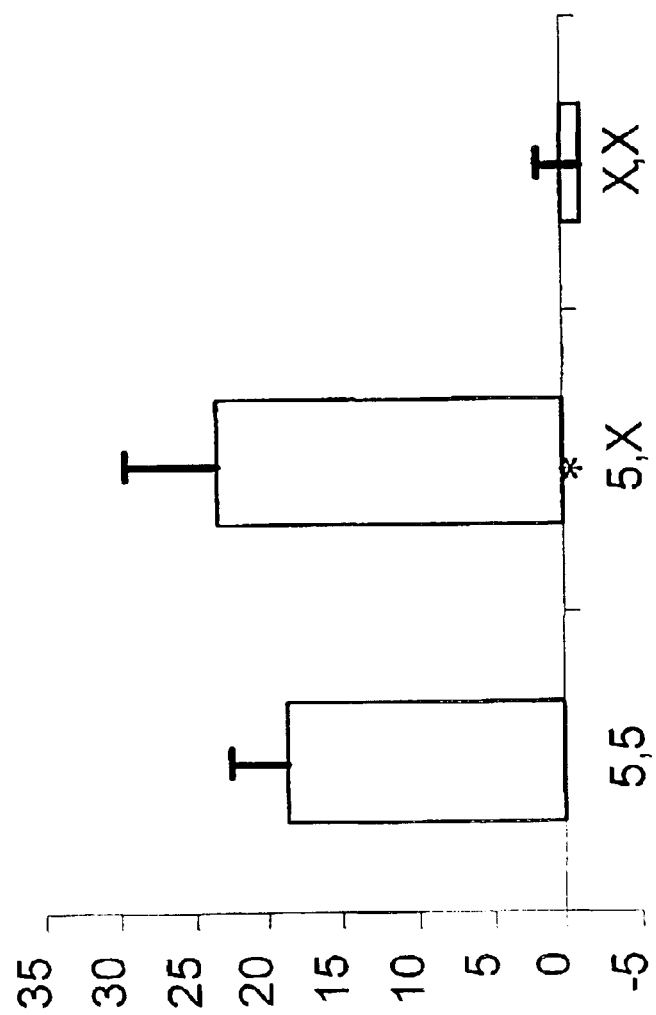
FIG. 1 is a graph showing the results of a previous study of the correlation between Sp1 polymorphisms at the ALOX5 gene alone and diminished response to the leukotriene synthesis inhibitor compound ABT-761 (Abbott Laboratories Inc., North Chicago, Ill.). The study was a randomized double-blind parallel-group trial (n=221) of clinically stable asthma patients, with $FEV_1$ of 40%–75% of predicted. ABT-761 was given at 150 and 300 mg/day. The vertical axis graphs the percent change in baseline $FEV_1$ after drug treatment; the horizontal axis provides genotypes (5,5= homozygous wild-type; 5,X=heterozygous wild-type; X,X= two non-wildtype alleles). Approximately 6% of the subjects were without the wild-type allele. The change in the variant group was significantly different from the 5,5 group (*$p<0.0001$).

The present inventors have determined that polymorphic variations in the ALOX5 gene and/or the LTC4S gene can be correlated to the response to pharmaceutical treatment, particularly treatment with leukotriene receptor antagonists, more particularly with CysLT1 leukotriene receptor antagonists, and also particularly with glucocorticoids. The present inventors have identified that there exists a single nucleotide polymorphism in the promoter region of enzyme LTC4 Synthase; an adenine to cytosine transversion 444 nucleotides upstream from the first codon, that is correlated with the response of subjects with asthma to treatment with a leukotriene receptor antagonist. They have further identified polymorphisms in the ALOX5 gene which are correlated with patient response. One such ALOX5 polymorphism is in the promoter region and contains 3 to 6 tandem repeats of the Sp-1 binding motif GGGCGG; individuals homozygous for the most commonly occurring allele (five tandem Sp1-binding motifs) are wild type, and individuals having 3, 4 or 6 tandem repeats of the Sp-1 binding motif are considered variant (i.e., non-wildtype). (Other numbers of tandem repeats may be found to be variant). Additional ALOX5 polymorphisms investigated include a G to A transversion polymorphism 1708 bases upstream from the first codon of the ALOX5 gene (G-1708A), and a single base transversion polymorphism 1728 bases downstream from the first codon (in exon 13) of the ALOX5 gene (A1728G or Pro576Pro). ALOX5 polymorphisms have also been found to be correlated with the response of subjects with asthma to treatment with a leukotriene receptor antagonist.

Little is known about the functionality of the LTC4 synthase promoter polymorphism, although an association with this allele and aspirin intolerant asthma has been published (Sanak, M et al Leukotriene C4 synthase promoter polymorphism and risk of aspirin-induced asthma. The Lancet 350;1599–1600, 1997). Applicants found a frequency of 57.6% homozygous wild type, 34.7% heterozygous, and 7.6% homozygous variant for this LTC4 synthase promoter polymorphism. These frequencies are similar to those found with the ALOX5 promoter polymorphism, yet the genes for these enzymes reside on different chromosomes.

As used herein, a "respiratory disorder that is potentially treatable" with a particular compound is one in which such treatment has been shown to be beneficial in a significant number of subjects suffering from that respiratory disorder. As will be apparent to those skilled in the art, a condition that is treatable with a certain compound or class of compounds does not imply that every patient so treated will benefit.

Polymorphisms may be present in the coding sequence of a gene, or in the 5' or 3' noncoding regions. The 5' noncoding region includes sequences important in transcriptional regulation, including promoters, negative regulatory regions, and positive regulatory regions.

Genetic samples were obtained from subjects enrolled in clinical trials for the treatment of asthma. The genetic samples were first screened for an adenine to cytosine transversion polymorphism 444 nucleotides upstream from the first codon in the leukotriene C4 Synthase gene (LTC4S gene), using polymerase chain reaction (PCR) technology. The alleles were labeled as "A" (adenine) or "C" (cytosine) resulting in three possible genotypes (A/A, A/C, and C/C The nucleotide sequence of human leukotriene C4 synthase (LTC4S) is provided in GenBank at accession number U50136 (SEQ ID NO:1):

```
  1  gagctcacag agcccccagc tggggcatat ctggtttccg ggggcagggg cgatacccag
 61  aggaggaaga agggattctg agagagccca acaggctccg agcctcaggc tggagctgag
121  cttggggcag caaggaagga ccaggtgcga gggcagaacc atgcggcccg acccctgcag
181  cacggcctgt ggcctccccc agctcctgcc cgtgcttctg ggtcagtctg gactttgcca
```

-continued

```
 241 cttctgacca aaagccaccg caaacccact caagccaaaa gaggaagtga ccgttaggcc
 301 caactgggaa ggctggcggc caggggcact ccaggcaggg cgaggggggc ggccggggc
 361 gctccagccg gggcgaggga gacacccaga actccaggca ggagtcctcg ggtgccacct
 421 ttcctctcca cctggccctg cgtgggctct gtcctcaggg tggcccgccg tagtcccct
 481 ccccactctg agtttcctgt cccaaagtcc taaggaagtt tccagaacta catctcacca
 541 tcttgagtca gccttggctc agtgtccatc tcacaggcct ggaaggggca ggagtcagca
 601 ctgtccagac cacagggcct gagtgtgggg agggcagccg tctaggaagg tggtggaggg
 661 ttgttacctt gaggcaagag ggctgcgggg cagaaagaca cagcaggtga ctgttgtggg
 721 aggcccaaga gaggcctggg agagggatgg cccacaaggg ctgaccctcc cgccacccag
 781 ggggccttgg acaggtttcc tcctggcagg gtggcccttg tgcatggaac cctacaacg
 841 actaaggctg gcaggcatga ggtttcctga aggagaaaga gcttgtgggg cccagtgtgg
 901 ctgggggggc gctgggactc cattctgaag ccaaaggcac tgggaagggc ttccgcagag
 961 gagggtttgg caggggttgc caggaacagc ctggatgggg acagggaaca gataaggtgg
1021 gtggaggagt tagccgggag cctggggctg gctccagcat gatgtggggg tctgcaaggc
1081 cctggagaaa gtggggtggt gcagcagggg gcacacccac agctggagct gacccagatg
1141 gacagcttgg gctctgccac gcgggactag gcaaggaagg ggcacgaaca agcaggaagt
1201 ggtgaggcgg tctccagcta gctgctctcc cctgcccaga ctttggtttc ctccctgctg
1261 gcttggcctg gctccctggc tctgtgtggt atggtcacac ccccgtgcac cccctccact
1321 gagatggggc ggggagagca ccgaggctgc tcttcctctc ctgggccgtc ctctgagcag
1381 cagacggggc taagcgttcc ccagctcgcc ttcacacaca gcccgtgcca ccacaccgac
1441 ggtaccatga aggacgaggt agctctactg gctgctgtca ccctcctggg agtcctgctg
1501 caaggtgggc tggttcctat ctaggaagag ggtgggcctt agatccctac agcttgccct
1561 ctgccccta ggcccaggtg gagggcagag gtggggactc cagcccaggc ccaagctgga
1621 agagggtggg gactttcagg gaactggggg gcacctggct gtgagagctg taggacttgg
1681 gggtggcaag ggtgccagga caaatggtag gatagccatg ggcttgggga agctgatctc
1741 tgctctttcc agctgtcccc tctctgggcg tcccagcaag cggcccccat tccctggctc
1801 tgcttcaaag gcacctccat actgggacca cgtggagcag ggtagaggtg ggactccttc
1861 ctccagcccc ctaaaaagag cctgcttaat gcctttctca gactggccct aaaggacaca
1921 ttccttggcc agatatcctt gccacctaag agacaccact actccacagt gtgtgggcta
1981 ggataaggca cagcctgggg aggggctct gaagggctg aacagacagg ccagcctgac
2041 ctccagctgc tcctgcactg agctggatgg ccaccctgtg cacccatct gcagagggcc
2101 cagaaccaaa ggtgccaggg ctgcaggact caggggaga tggtccgacg ggaggtctgg
2161 ggagggagcg cacagccagc actggtctgt gtgtggtctg cctggcctc acctgaccaa
2221 gagaagggct cctgcccaca gagaaacttt agggccagcc caccctctgc aactacccca
2281 gccctgggt cctggggtta ggctaggaga gtcccagctg caacctcctg ggagcaggag
2341 agaaggtgtc tgtcagattt aggcctggga ccggaatgca ggaacagaga aactgaggtt
2401 tggaggcaca gggacgcagg ctttagtgat cccggcctga ggcagggtca gagggccctg
2461 ctggtgggcg ctggtaggtg ggtgaccagg gactgttagc tacagggagt gtgcttcctt
2521 gcacctggga ggatgcagcc agctctgccc tcagactccc gaggcacttc ctggccaggg
2581 acctgaaagc tgcatttgcc tgtgttttga gagtgaaatg attcagaaac aaggactcaa
```

-continued

```
2641 gtggtctctc tcgcggagca ggtgtccctg tgcctgaatc actcaccctc ccccatacac 2701 tcacaggttg ggacagggcc tctctgcgcc ccaggcttca gccctgccct cctcgctgaa 2761 tgtcagggac acagggcagg ccaggdatgg gtgagacgag aggtctcctc gggcggggag 2821 ggggcggggt tccgccttag ggaggagagg acacggccaa gtgaagggcc agattgcagg 2881 atccctccca ctcccatctc tggggcttcg ggtgtccaga cctgactccc gctcccctc 2941 ctccccagc ctacttctcc ctgcaggtga tctcggcgcg cagggccttc cgcgtgtcgc 3001 cgccgctcac caccggccca cccgagttcg agcgcgtcta ccgagcccag tgaggcgcgg 3061 cgggagggcg cggggcgggg agcgagcccc aggcgggtcc gggtcgcagg accatcccgg 3121 ccggcgcgct catcccaccc gcccaccgca gggtgaactg cagcgagtac ttcccgctgt 3181 tcctcgccac gctctgggtc gccggcatct tctttcatga aggtcggggt gtggggcagg 3241 ggcgcacgcg ctggaccccc gggacccgcg cagggcgctc accaggcccg tgcgtacctc 3301 tcgcaggggc ggcggccctg tgcggcctgg tctacctgtt cgcgcgcctc cgctacttcc 3361 agggctacgc gcgctccgcg cagctcaggt gagggccggg cggggagcgg ggcggggccg 3421 gggaaagatc gcgggcgggc ggggctcctg gggagcggga ccgaagctgg gggcgggcga 3481 cgggccggag cccagcgcct ttggggattc ggtgggcgag ccctggcggc ggccagagga 3541 agtccccgtg gggccagggt tgcggcgggg aagaagcggg cctcctcgcg ccacctcccc 3601 gctgaccgcc gcccgcaggc tggcaccgct gtacgcgagc gcgcgcgccc tctggctgct 3661 ggtggcgctg gctgcgctcg gcctgctcgc ccacttcctc ccggccgcgc tgcgcgccgc 3721 gctcctcgga cggctccgga cgctgctgcc gtgggcctga gaccaaggcc cccgggccga 3781 cggagccggg aaagaagagc cggagcctcc agctgccccg gggaggggcg ctcgcttccg 3841 catcctagtc tctatcatta aagttctagt gaccgagacc cgggctgcgt tctctgggtc 3901 cgcggggtg gcgcaccgcg ggctacggag cctggagggg cccagcccga gtccgggcag 3961 cccggggcgg gcttcctagt ggcggcgtga gagtggctgc gaaggaacga gccctccccc 4021 tggggcggga ctggatccgg tcttcacctc ctaccccact ccctactcag cctcgggtc 4081 acaaggccgc ccagtcctgc cggggttcac cctcctagcg ctcagcggtc tcctcaccgg 4141 tccccctcct caggggcctt ccctcgactc tcagccgccg cagtccctcg tccctggcc 4201 ttcacagctg acactagata gagcctgtgg ctctctcccc aggtgagggc aggggttttt 4261 cttttggtca gcactggatc cccctcgtta actgtaggtg ttcagggcag ccctccgagg 4321 tccgcagagc tgcgggcacc atgggaacga agtgagtcag tgacaggcgg tctcaaggaa 4381 atgtccagaa gccttgggga tccaggggag gcccacagaa acaaagaagt gacttttagc 4441 caagtatgca ggagaaacgg aggag
```

The protein encoded by the above is provided at SEQ ID NO:2.

An adenine to cytosine transversion polymorphism (A-444C) is known at the position 444 nucleotides upstream (bold and underlined, above) from the first codon (underlined, above). Accordingly, the "A" allele as defined herein would comprise the sequence CTGGATGGGG AC AGGGAACA (SEQ ID NO:3) (nucleotides 991–1010 of SEQ ID NO:1). In contrast, the "C" allele as defined herein would comprise the sequence CTGGATGGGG AC CGGGAACA (SEQ ID NO:4) (nucleotides corresponding to 991–1010 of SEQ ID NO:1).

The genetic samples were secondly screened for a polymorphism in the region of 176 to 147 base pairs upstream from the ATG start site in 5-lipoxygenase (ALOX5), whereby the presence of 5 tandem repeats of the Sp1 binding motif (GGGCGG; SEQ ID NO:12) is wildtype, and the presence of 3, 4 or 6 such tandem repeats is variant, again using PCR technology. The alleles were labeled as "5" (5 tandem repeats) or "X" (3, 4 or 6 tandem repeats), resulting in three possible genotypes (5,5, 5/X and X/X). Variant ALOX5 alleles have a number of tandem repeats of the Sp1 binding motif in this region that is more than, or fewer than, five repeats. That is, in the region of from about 200 nucleotides to about 125 nucleotides upstream of the ATG start site in ALOX5, there are from one to four, or more than five, repeats of the Sp1 binding motif. In the present studies, variant ALOX5 alleles ("X") had three, four or six tandem repeats in this area.

Screening was also conducted for a G to A transversion polymorphism 1708 bases upstream from the first codon of the ALOX5 gene (G-1708A), and for a single base transversion polymorphism 1728 bases downstream from the first codon (in exon 13) of the ALOX5 gene (A1728G).

The nucleotide sequence of the 5' region and partial coding sequence of human 5-lipoxygenase (ALOX5) containing five repeats of the Sp1 binding motif, and the G-1708A polymorphism, is provided at GenBank Accession number M38191(SEQ ID NO:5):

```
   1 ggatccagaa taaccaaaac aatattgaaa aataaagaac agcgttggtg gattaacatt
  61 ttccaatttc aaaacttact atagcactgc ggtaatcaag cagtgtggca ctgtatagca
 121 tgtacattac agatcagtgg actagaatca atgtccagaa ataaaccgtt atgtttataa
 181 tgaattactt tttaataagg tgtcaagaca acgcaatggg aaaagaataa tgaattcaac
 241 aaatgatgca tggacaaccg gacatgcaca tgcaacacaa tgaatttgaa ttcttctatc
 301 gctccatgca taaaaactaa ctcaaaatgg gtcacggatg taaatgaaaa gctaaaacta
 361 taataatcct agaggaaaac ctaggagtaa atctttaaga tgttattgta ggcagtggtt
 421 tctcagatag gaccccaaaa tcacaagcga caaaaagaaa ttggacttaa agttaaatac
 481 ttttgtgctt caaacatcat caagaaagtg aaaacacaac ccgcagaagc aataaaaatg
 541 tctgtaagtc atgtatccga ttagagactt ctatccagga tatataaata atgcaattca
 601 atgataaaaa agataaaatag cccagttttc caaagagtca agcatctgaa tatacatctc
 661 tccaaaaata tacagatatc caacaagcat gtgaaaagat gttcaaagcc atttgccagg
 721 tgcacaaacc caagacagta tgaggagatg ctacagggac tctgctgctt cacagacatg
 781 aagcgttggt gagaatgtag gcagccgcct ttggggactt cacatccccg ccgccccacg
 841 cacggtgagc tagtgtttaa acttagccga gatcaataca cgcgactgtg tgcccgtcag
 901 accctgcgct gccggcgggg ctgggagagg cgggcgccag gagtgggcgg gaacctgggg
 961 gtcaggcccc agccgcggga agcgcgccca ggagcgcgcg aaaccttctc cacacccttc
1021 caggcatttg cccgccgcga ttcagagagc cgaccccgtga ccctggcct cccctagaca
1081 gccccgcatg tccagatgtg ccgtcccgcc tgcctcccgc gaccactggc catctctggg
1141 cctgggcgcg gttctcggcg cccggcctgc ccccgccagg agccgcaggt ccagccagtg
1201 aagaagcccg cgcctgaagg agcctctgtg ctccagaatc catcctcagt atcagcgctg
1261 gggtggcctc ctccaggaag cccttctgat tctctcatgg gtcgctcttc ctctgcagac
1321 tcccggagca cccctgctc caagtaccgc aagtggcact gagaacttgg ggagagcaga
1381 ggctgtgcct agatttgtag ggagtccccg cagctccacc ccagggccta caggagcctg
1441 gccttgggcg aagccgaggc aggcaggcag ggcaaagggt ggaagcaatt caggagagaa
1501 cgagtgaacg aatggatgag gggtggcagc cgaggttgcc ccagtcccct ggctgcagga
1561 acagacacct cgctgaggag agacccagga gcgaggcccc tgcccgccc gaggcgaggt
1621 cccgcccagt cggcgccgcg cgtgaagagt gggagagaag tactgcggga gcggggcgg
1681 gggcggggc ggggcggggg gcagccggga gcctggagcc agaccggggc ggggccggga
1741 ccggggccag ggaccagtgg tgggaggagg ctgcggcgct agatgcggac acctggaccg
1801 ccgcgccgag gctccggcg ctcgctgctc ccgcggcccg cgccatgccc tcctacacgg
1861 tcaccgtggc cactgcagc cagtggttcg ccggcactga cgactacatc tacctcagcc
1921 tcgtgggctc ggcgggctgc agcgagaagc acctgctgga caagcccttc tacaacgact
1981 tcgagcgtgg cgcggtgagc gcgggcgggg cacgggtgga gcgcgggctg aggtgcgtcc
2041 gggacccggt ttggacggca gaggcctggg cggggcgcc gagggcccgt cggggcggcc
2101 cggacaggac tgggggtgtc caggaccctg tcagggaggg cagaactgcg gtggggcgtg
2161 ccctgggctc ccagtggccg gtgggtacc
```

The first codon is underlined; the region comprising the repeats of the Sp1 binding motif (GGGCGG) is shown in bold and underlined type; the G-1708A position is also shown in bold and underlined type.

The 5-lipoxygenase gene has been cloned as cDNA (Matsumoto et al., *Proc. Natl. Acad. Sci. USA* 85:3406 (1988)) and as a genomic clone (Hoshiko et al., *Proc. Natl. Acad. Sci. USA* 87:9073 (1990). The 5-lipoxygenase gene is approximatly 85 kilobases in size, with 14 exons and 15 introns.

Two ALOX5 mRNA sequences are provided in GenBank at Accession numbers NM 000698 and XM 005818. The sequence provided at NM 000698 encodes a protein of 674 amino acids and is shown below:

(SEQ ID NO:13)

```
   1 gggcgccgag gctccccgcc gctcgctgct ccccggcccg cgccatgccc tcctacacgg
  61 tcaccgtggc cactggcagc cagtggttcg ccggcactga cgactacatc tacctcagcc
 121 tcgtgggctc ggcgggctgc agcgagaagc acctgctgga caagcccttc tacaacgact
 181 tcgagcgtgg cgcggtggat tcatacgacg tgactgtgga cgaggaactg ggcgagatcc
 241 agctggtcag aatcgagaag cgcaagtact ggctgaatga cgactggtac ctgaagtaca
 301 tcacgctgaa gacgccccac ggggactaca tcgagttccc ctgctaccgc tggatcaccg
 361 gcgatgtcga ggttgtcctg agggatggac gcgcaaagtt ggcccgagat gaccaaattc
 421 acattctcaa gcaacaccga cgtaaagaac tggaaacacg gcaaaaacaa tatcgatgga
 481 tggagtggaa ccctggcttc cccttgagca tcgatgccaa atgccacaag gatttacccc
 541 gtgatatcca gtttgatagt gaaaaaggag tggactttgt tctgaattac tccaaagcga
 601 tggagaacct gttcatcaac cgcttcatgc acatgttcca gtcttcttgg aatgacttcg
 661 ccgactttga gaaaatcttt gtcaagatca gcaacactat ttctgagcgg gtcatgaatc
 721 actggcagga agacctgatg tttggctacc agttcctgaa tggctgcaac cctgtgttga
 781 tccggcgctg cacagagctg cccgagaagc tcccggtgac cacggagatg gtagagtgca
 841 gcctggagcg gcagctcagc ttggagcagg aggtccagca agggaacatt ttcatcgtgg
 901 actttgagct gctggatggc atcgatgcca acaaaacaga cccctgcaca ctccagttcc
 961 tggccgctcc catctgcttg ctgtataaga acctggccaa caagattgtc cccattgcca
1021 tccagctcaa ccaaatcccg ggagatgaga accctatttt cctcccttcg gatgcaaaat
1081 acgactggct tttggccaaa atctgggtgc gttccagtga cttccacgtc caccagacca
1141 tcacccacct tctgcgaaca catctggtgt ctgaggtttt tggcattgca atgtaccgcc
1201 agctgcctgc tgtgcacccc attttcaagc tgctggtggc acacgtgaga ttcaccattg
1261 caatcaacac caaggcccgt gagcagctca tctgcgagtg tggcctcttt gacaaggcca
1321 acgccacagg gggcggtggg cacgtgcaga tggtgcagag ggccatgaag gacctgacct
1381 atgcctccct gtgctttccc gaggccatca ggcccggggg catggagagc aaagaagaca
1441 tcccctacta cttctaccgg gacgacgggc tcctggtgtg ggaagccatc aggacgttca
1501 cggccgaggt ggtagacatc tactacgagg gcgaccaggt ggtggaggag gacccggagc
1561 tgcaggactt cgtgaacgat gtctacgtgt acgcatgcg ggccgcaag tcctcaggct
1621 tccccaagtc ggtcaagagc cgggagcagc tgtcggagta cctgaccgtg gtgatcttca
1681 ccgcctccgc ccagcacgcc gcggtcaact cggccagta cgactggtgc tcctggatcc
1741 ccaatgcgcc cccaaccatg cgagccccgc caccgactgc caagggcgtg gtgaccattg
1801 agcagatcgt ggacacgctg cccgaccgcg gccgctcctg ctggcatctg ggtgcagtgt
1861 gggcgctgag ccagttccag gaaaacgagc tgttcctggg catgtaccca gaagagcatt
1921 ttatcgagaa gcctgtgaag gaagccatgg cccgattccg caagaacctc gaggccattg
1981 tcagcgtgat tgctgagcgc aacaagaaga agcagctgcc atattactac ttgtccccag
2041 accggattcc gaacagtgtg gccatctgag cacactgcca gtctcactgt gggaaggcca
```

-continued

```
2101 gctgccccag ccagatggac tccagcctgc ctggcaggct gtctggccag gcctcttggc 2161 agtcacatct cttcctccga ggccagtacc tttccattta ttctttgatc ttcagggaac 2221 tgcatagatt gtatcaaagt gtaaacacca tagggaccca ttctacacag agcaggactg 2281 cacaggcgtc ctgtccacac ccagctcagc atttccacac caagcagcaa cagcaaatca 2341 cgaccactga tagatgtcta ttcttgttgg agacatggga tgattatttt ctgttctatt 2401 tgtgcttagt ccaattcctt gcacatagta ggtacccaat tcaattacta ttgaatgaat 2461 taagaattgg ttgccataaa aataaatcag ttcattt
```

The 1728 polymorphism site is indicated in underlined and bolded type; the A1728G polymorphism does not change the encoded amino acid (proline at amino acid position 576; SEQ ID NO: 14).

The sequence at XM 005818 is provided below (SEQ ID NO:15) and encodes an amino acid sequence (SEQ ID NO:16) that differs from that encoded by NM000698 in the initial amino acids. The site of the A1728G polymorphism (numbering referenced to NM000698) is shown in underlined bold type.

```
                                                                (SEQ ID NO:15)
   1 cttcacccg tggtgaagac actgacgact acatctacct cagcctcgtg ggctcggcgg 61 gctgcagcga gaagcacctg ctggacaagc ccttctacaa cgacttcgag cgtggcgcgg 121 tggattcata cgacgtgact gtggacgagg aactgggcga gatccagctg gtcagaatcg 181 agaagcgcaa gtactggctg aatgacgact ggtacctgaa gtacatcacg ctgaagacgc 241 cccacgggga ctacatcgag ttcccctgct accgctggat caccggcgat gtcgaggttg 301 tcctgaggga tggacgcgca aagttggccc gagatgacca aattcacatt ctcaagcaac 361 accgacgtaa agaactggaa acacggcaaa aacaatatcg atggatggag tggaaccctg 421 gcttcccctt gagcatcgat gccaaatgcc acaaggattt accccgtgat atccagtttg 481 atagtgaaaa aggagtggac tttgttctga attactccaa agcgatggag aacctgttca 541 tcaaccgctt catgcacatg ttccagtctt cttggaatga cttcgccgac tttgagaaaa 601 tctttgtcaa gatcagcaac actatttctg agcgggtcat gaatcactgg caggaagacc 661 tgatgtttgg ctaccagttc ctgaatggct gcaaccctgt gttgatccgg cgctgcacag 721 agctgcccga gaagctcccg gtgaccacgg agatggtaga gtgcagcctg gagcggcagc 781 tcagcttgga gcaggaggtc cagcaaggga acattttcat cgtggacttt gagctgctgg 841 atggcatcga tgccaacaaa acagacccct gcacactcca gttcctggcc gctcccatct 901 gcttgctgta taagaacctg gccaacaaga ttgtccccat tgccatccag ctcaaccaaa 961 tcccgggaga tgagaaccct atttttcctcc cttcggatgc aaaatacgac tggcttttgg 1021 ccaaaatctg ggtgcgttcc agtgacttcc acgtccacca gaccatcacc caccttctgc 1081 gaacacatct ggtgtctgag gttttttggca ttgcaatgta ccgccagctg cctgctgtgc 1141 accccatttt caagctgctg gtggcacacg tgagattcac cattgcaatc aacaccaagg 1201 cccgtgagca gctcatctgc gagtgtggcc tctttgacaa ggccaacgcc acaggggggcg 1261 gtgggcacgt gcagatggtg cagagggcca tgaaggacct gacctatgcc tccctgtgct 1321 ttcccgaggc catcaaggcc cggggcatgg agagcaaaga agacatcccc tactacttct 1381 accgggacga cgggctcctg gtgtgggaag ccatcaggac gttcacggcc gaggtggtag
```

-continued

```
1441  acatctacta cgagggcgac caggtggtgg aggaggaccc ggagctgcag gacttcgtga 1501  acgatgtcta cgtgtacggc atgcggggcc gcaagtcctc aggcttcccc aagtcggtca 1561  agagccggga gcagctgtcg gagtacctga ccgtggtgat cttcaccgcc tccgcccagc 1621  acgccgcggt caacttcggc cagtacgact ggtgctcctg gatccccaat gcgcccccaa 1681  ccatgcgagc cccgccaccg actgccaagg gcgtggtgac cattgagcag atcgtggaca 1741  cgctgcccga ccgcggccgc tcctgctggc atctgggtgc agtgtgggcg ctgagccagt 1801  tccaggaaaa cgagctgttc ctgggcatgt acccagaaga gcattttatc gagaagcctg 1861  tgaaggaagc catgcccga ttccgcaaga acctcgaggc cattgtcagc gtgattgctg 1921  agcgcaacaa gaagaagcag ctgccatatt actacttgtc cccagaccgg attccgaaca 1981  gtgtggccat ctgagcacac tgccagtctc actgtgggaa ggccagctgc cccagccaga 2041  tggactccag cctgcctggc aggctgtctg gccaggcctc ttggcagtca catctcttcc 2101  tccgaggcca gtacctttcc atttattctt tgatcttcag ggaactgcat agattgatca 2161  aagtgtaaac accataggga cccattctac acagagcagg actgcacagc gtcctgtcca 2221  cacccagctc agcatttcca caccaagcag caacagcaaa tcacgaccac tgatagatgt 2281  ctattcttgt tggagacatg ggatgattat tttctgttct atttgtgctt agtccaattc 2341  cttgcacata gtaggtaccc aattcaatta ctattgaatg aattaagaat tggttgccat 2401  aaaaataaat cagttcattt
```

The present inventors have determined that the C/C genotype at the A-444C site of LTC4S, the X/X Sp1 genotype in ALOX5, and the polymorphism at the A1728G site of ALOX5 are independently associated with diminished response to the Cys LT1 leukotriene receptor antagonist zafirlukast.

According to the present methods, a subject who suffers from asthma that is potentially treatable with an anti-inflammatory inhaled glucocorticoid or a leukotriene antagonist, is genetically screened, to aid in predicting their response to such treatment. Screening comprises obtaining a sample of DNA from the subject and screening the DNA to determine the genotype (presence/absence of polymorphic alleles) at a predetermined polymorphic site in the gene of interest (here ALOX5 and/or LTC4S polymorphisms as described), where different genotypes at that site have previously been associated with different incidences of a phenotypic response to treatment. The presence of a particular genotype therefore indicates an increased likelihood that the individual subject will exhibit the associated phenotype. The genotype will rarely be absolutely predictive, i.e., where a population with a certain genotype displays a high incidence of a particular phenotype, not every individual with that genotype will display the phenotype. However, it will be apparent to those skilled in the art that genotyping a subject as described herein will be an aid in predicting the response a subject will have to treatment with a leukotriene receptor antagonist or a glucocorticoid, and thus assist in the treatment decision.

As used herein, "genotyping a subject (or DNA sample) for a polymorphic allele at a defined genomic locus" or "determining the genotype at a polymorphic allelic site" means detecting which forms of the allele are present in a subject (or a biological sample). As is well known in the art, an individual may be heterozygous or homozygous for a particular allele. More than two forms of an allele may exist, as is the case with microsatellite markers; thus there may be more than three possible genotypes.

As used herein, a subject that is "predisposed to" a particular phenotypic response based on genotyping of a polymorphic allele will be more likely to display that phenotype than an individual with a different genotype at that polymorphic allele. Where the phenotypic response is based on a biallelic polymorphism, the response may differ among the three possible genotypes (Eg. For LTC4S: A,A; A,C and C,C).

As used herein, a "genetic subset" of a population consists of those members of the population having a particular genotype. In the case of a biallelic polymorphism, a population can potentially be divided into three subsets: homozygous for allele 1, heterozygous, and homozygous for allele 2. Where multiple non-wildtype polymorphisms exist, a population can also be divided into three subsets: homozygous wildtype; heterozygous wildtype; and homozygous non-wildtype.

As used herein, asthma treatable with an anti-inflammatory glucocorticoid or treatable with a leukotriene receptor antagonist is a disease in which the administration of such a drug (in an appropriate pharmaceutical formulation, and in a therapeutically effective amount) has been shown to reduce or alleviate symptoms, without causing unacceptable side effects. Such therapeutic effectiveness is typically evidenced by Regulatory Authority (eg FDA, EMEA) approval of the pharmaceutical preparation, or by publication of the results of clinical studies in peer-reviewed medical journals. Therapeutically effective amounts of such compounds can be readily determined by those skilled in the art using, e.g., dose-response studies.

Known leukotriene receptor antagonists include zafirlukast, montelukast, pranlukast or iralukast.

As used herein, a "side effect" is an undesirable response to the administration of a therapeutic compound, e.g., an effect that is not directed to alleviating the symptoms or cause of the disease being treated. Side effects range from minor inconveniences to more serious events.

As used herein, "response" to treatment with a therapeutic compound is a desirable response to the administration of the compound, e.g., alleviation of the symptoms of the disease or of the underlying pathologic causes of the symptoms. Various indicators of a subject's response to therapeutic treatment may be assessed, as will be apparent to one skilled in the art. As an example, the change in Forced Expiratory Volume (FEV; $FEV_1$=FEV for 1 second duration) may be used as an indicator of response to treatment for asthma, as will be apparent to one skilled in the art.

According to the present methods, a compound with leukotriene receptor antagonism may be screened for variation in its effects among genetic subpopulations of subjects with asthma. Such methods involve administering the compound alone, or in tandem with another anti-asthma compound (such as a glucocorticoid), to a population of subjects suffering from asthma, obtaining DNA samples from the subjects (which may be done either prior to or after administration of the compounds), genotyping a polymorphic allelic site in the gene of interest, and correlating the genotype of the subjects with their phenotypic responses (both favorable and unfavorable) to the treatment. A genotype that is correlated with an increased incidence of a desired therapeutic response, compared to the incidence in subjects with alternative genotypes at the polymorphic allelic site, indicates that the effectiveness of the compound in treating asthma varies among genetic subpopulations.

Stated another way, the methods of the present invention may be used to determine the correlation of a known polymorphic allele with the response of subjects to treatment with a leukotriene receptor antagonist or a glucocorticoid. The population of subjects with the disease of interest is stratified according to genotype for the particular polymorphic allele, and their response to a therapeutic agent is assessed (either prospectively or retrospectively) and compared among the genotypes. The response to the therapeutic agent may include either, or both, desired therapeutic responses (e.g., the alleviation of signs or symptoms) and undesirable side effects. In this way, genotypes that are associated with an increased (or decreased) incidence of therapeutic efficacy, or an increased (or decreased) incidence of a particular side effect, may be identified. The increase or decrease in response is in comparison to the other genotypes, or to a population as a whole.

Polymorphisms are variant sequences within the human genome that may or may not have a functional consequence. These variants can be used in all aspects of genetic investigation including the analysis and diagnosis of genetic disease, forensics, evolutionary and population studies. Two types of genetic analyses are typically performed: linkage and association studies.

A linkage study provides genetic map information with no prior knowledge or assumption about the function of a gene. In a linkage study one uses DNA polymorphisms to identify chromosomal regions that are identical between affected relatives with the expectation that allele sharing frequencies will be higher for a marker (polymorphism) whose chromosomal location is close to that of the disease allele. Physical cloning of a linkage region narrows down the DNA sequence that could harbor the candidate disease gene. While linkage analysis locates the disease locus to a specific chromosome or chromosome region, the region of DNA in which to search for the gene is typically large, on the order of several million base pairs.

In contrast to linkage, association shows the coexistence of a polymorphism and a disease phenotype in a population. Association studies are based upon linkage disequilibrium, a phenomenon that occurs between a marker and a disease loci when the occurrence of two alleles at different loci is larger than the product of the allelic frequencies. Since the marker and disease causing variant are in close proximity, it requires many generations of recombination to separate them in a population. Thus they tend to co-exist together on the same chromosome at a higher than expected frequency. A marker (polymorphism) is said to be associated with a specific phenotype when its frequency is significantly higher among one phenotype group compared to its frequency in another. In general, the closer a marker is to the functionally polymorphic site, the stronger the association.

Association studies offer the opportunity to finely map linkage regions, map loci refractory to linkage analysis and map unknown predisposition loci. Polymorphisms that are in linkage disequilibrium with each other can be spaced over large regions. Linkage disequilibrium has been reported in regions as small as 1 kb or as large as 500 kb. Polymorphisms throughout a gene can be in linkage disequilibrium with each other, such that it is valuable to study the whole genome structure—introns, exons, promoters and transcriptional regulatory regions, and 3' and 5' untranslated regions. A marker that is in linkage disequilibrium with a functional polymorphism can be tested for correlation with a phenotype.

As used herein, the term polymorphism includes Single Nucleotide Polymorphisms (SNPs), insertion/deletion polymorphisms; transversion polymorphisms; microsatellite polymorphisms; and variable number of tandem repeat (VNTR) polymorphisms.

Polymorphic alleles are typically detected by directly determining the presence of the polymorphic sequence in a polynucleotide or protein from the subject, using any suitable technique as is known in the art. Such a polynucleotide is typically genomic DNA, or a polynucleotide derived from this polynucleotide, such as in a library made using genomic material from the individual (e.g. a cDNA library). The processing of the polynucleotide or protein before the carrying out of the method of the invention is further discussed below. Typically the presence of the polymorphism is determined in a method that comprises contacting a polynucleotide or protein of the individual with a specific binding agent for the polymorphism and determining whether the agent binds to the polynucleotide or protein, where the binding indicates that the polymorphism is present. The binding agent may also bind to flanking nucleotides and amino acids on one or both sides of the polymorphism, for example at least 2, 5, 10, 15 or more flanking nucleotide or amino acids in total or on each side. In one embodiment the agent is able to bind the corresponding wild-type sequence by binding the nucleotides or amino acids which flank the polymorphism position, although the manner of binding will be different than the binding of a polymorphic polynucleotide or protein, and this difference will be detectable (for example this may occur in sequence specific PCR as discussed below).

In the case where the presence of the polymorphism is being determined in a polynucleotide it may be detected in the double stranded form, but is typically detected in the single stranded form.

The binding agent may be a polynucleotide (single or double stranded) typically with a length of at least 10 nucleotides, for example at least 15, 20, 30, or more polynucleotides. The agent may be a molecule that is a structurally similar polynucleotide that comprises units (such as purines or pyrimidines) able to participate in Watson-Crick base pairing. The agent may be a protein, typically with a length of at least 10 amino acids, such as at least 20, 30, 50, 100 amino acids. The agent may be an antibody (including a fragment of such an antibody that is capable of binding the polymorphism).

A polynucleotide agent which is used in the method will generally bind to the polymorphism of interest, and the flanking sequence, in a sequence specific manner (e.g. hybridize in accordance with Watson-Crick base pairing) and thus typically has a sequence which is fully or partially complementary to the sequence of the polymorphism and flanking region.

In one embodiment of the present methods a binding agent is used as a probe. The probe may be labeled or may be capable of being labeled indirectly. The detection of the label may be used to detect the presence of the probe on (and hence bound to) the polynucleotide or protein of the individual. The binding of the probe to the polynucleotide or protein may be used to immobilize either the probe or the polynucleotide or protein (and thus to separate it from one composition or solution).

In another embodiment of the invention the polynucleotide or protein of the individual is immobilized on a solid support and then contacted with the probe. The presence of the probe immobilized to the solid support (via its binding to the polymorphism) is then detected, either directly by detecting a label on the probe or indirectly by contacting the probe with a moiety that binds the probe. In the case of detecting a polynucleotide polymorphism the solid support is generally made of nitrocellulose or nylon. In the case of a protein polymorphism the method may be based on an ELISA system.

The present methods may be based on an oligonucleotide ligation assay in which two oligonucleotide probes are used. These probes bind to adjacent areas on the polynucleotide which contains the polymorphism, allowing (after binding) the two probes to be ligated together by an appropriate ligase enzyme. However the two probes will only bind (in a manner which allows ligation) to a polynucleotide that contains the polymorphism, and therefore the detection of the ligated product may be used to determine the presence of the polymorphism.

In one embodiment the probe is used in a heteroduplex analysis based system to detect polymorphisms. In such a system when the probe is bound to a polynucleotide sequence containing the polymorphism it forms a heteroduplex at the site where the polymorphism occurs (i.e. it does not form a double strand structure). Such a heteroduplex structure can be detected by the use of an enzyme that is single or double strand specific. Typically the probe is an RNA probe and the enzyme used is RNAse H that cleaves the heteroduplex region, thus allowing the polymorphism to be detected by means of the detection of the cleavage products.

The method may be based on fluorescent chemical cleavage mismatch analysis which is described for example in PCR Methods and Applications 3:268–71 (1994) and Proc. Natl. Acad. Sci. 85:4397–4401 (1998).

In one embodiment the polynucleotide agent is able to act as a primer for a PCR reaction only if it binds a polynucleotide containing the polymorphism (i.e. a sequence—or allele-specific PCR system). Thus a PCR product will only be produced if the polymorphism is present in the polynucleotide of the individual. Thus the presence of the polymorphism may be determined by the detection of the PCR product. Preferably, the region of the primer which is complementary to the polymorphism is at or near the 3' end of the primer. In one embodiment of this system the polynucleotide the agent will bind to the wild-type sequence but will not act as a primer for a PCR reaction.

The method may be an Restriction Fragment Length Polymorphism (RFLP) based system. This can be used if the presence of the polymorphism in the polynucleotide creates or destroys a restriction site that is recognized by a restriction enzyme. Thus treatment of a polynucleotide with such a polymorphism will lead to different products being produced compared to the corresponding wild-type sequence. Thus the detection of the presence of particular restriction digest products can be used to determine the presence of the polymorphism.

The presence of the polymorphism may be determined based on the change that the presence of the polymorphism makes to the mobility of the polynucleotide or protein during gel electrophoresis. In the case of a polynucleotide single-stranded conformation polymorphism (SSCP) analysis may be used. This measures the mobility of the single stranded polynucleotide on a denaturing gel compared to the corresponding wild-type polynucleotide, the detection of a difference in mobility indicating the presence of the polymorphism. Denaturing gradient gel electrophoresis (DGGE) is a similar system where the polynucleotide is electrophoresed through a gel with a denaturing gradient, a difference in mobility compared to the corresponding wild-type polynucleotide indicating the presence of the polymorphism.

The presence of the polymorphism may be determined using a fluorescent dye and quenching agent-based PCR assay such as the Taqman PCR detection system. In brief, this assay uses an allele specific primer comprising the sequence around, and including, the polymorphism. The specific primer is labeled with a fluorescent dye at its 5' end, a quenching agent at its 3' end and a 3' phosphate group preventing the addition of nucleotides to it. Normally the fluorescence of the dye is quenched by the quenching agent present in the same primer. The allele specific primer is used in conjunction with a second primer capable of hybridizing to either allele 5' of the polymorphism.

In the assay, when the allele comprising the polymorphism is present Taq DNA polymerase adds nucleotides to the nonspecific primer until it reaches the specific primer. It then releases polynucleotides, the fluorescent dye and quenching agent from the specific primer through its endonuclease activity. The fluorescent dye is therefore no longer in proximity to the quenching agent and fluoresces. In the presence of the allele which does not comprise the polymorphism the mismatch between the specific primer and template inhibits the endonuclease activity of Taq and the fluorescent dye in not released from the quenching agent. Therefore by measuring the fluorescence emitted the presence or absence of the polymorphism can be determined.

In another method of detecting the polymorphism a polynucleotide comprising the polymorphic region is sequenced across the region which contains the polymorphism to determine the presence of the polymorphism.

Accordingly, any of the following techniques may be utilized in the present methods for genotyping, as is known in the art.

General: DNA sequencing, sequencing by hybridization;

Scanning: PTT (Protein truncation technique), SSCP (single strand conformational analysis), DGGE (denaturing gradient gel electrophoresis), TGGE (temperature gradient gel electrophoresis), Cleavase, Heteroduplex analysis, CMC (chemical mismatch cleavage), enzymatic mismatch cleavage;

Hybridization based: solid phase hybridization (dot blots, MASDA, reverse dot blots, oligonucleotide arrays (chips)); solution phase hybridization (Taqman, Molecular Beacons);

Extension based: ARMS (Amplification Refractory Mutation System), ALEX (Amplification Refractory Mutation System Linear Extension) SBCE (Single Base Chain Extension)

Incorporation based: Mini-sequencing, APEX; (Arrayed Primer Extension)

Restriction enzyme based: RFLP (restriction fragment length polymorphism)

Ligation based: OLA (Oligonucleotide Extension Assay)

Other: Invader (Third Wave Technologies).

The present invention also provides for a predictive (patient care) test or test kit. This predictive test could be a product and/or a service which aids in disease management of asthma based on pre-determined associations between genotype and phenotypic response to leukotriene receptor antagonists in treating asthma. Such a test could take two different formats:

A) a molecular test which analyses DNA or RNA for the presence of pre-determined polymorphisms. An appropriate test kit may include one or more of the following reagents or instruments: a means to detect the binding of the agent to the polymorphism, an enzyme able to act on a polynucleotide (typically a polymerase or restriction enzyme), suitable buffers for enzyme reagents, PCR primers which bind to regions flanking the polymorphism, a positive or negative control (or both), a gel electrophoresis apparatus and a means to isolate DNA from a sample. The product may utilise one of the chip technologies as described by the current state of the art. The test kit would include printed or machine readable instructions setting forth the correlation between the presence of a specific polymorphism or genotype and the likelihood that a subject with asthma will respond favorably to therapy with a leukotriene receptor antagonist; or B) a biochemical test which analyses materials derived from the subject's body, including proteins or metabolites, that indicate the presence of a pre-determined polymorphism. An appropriate test kit would comprise a molecule, aptamer, peptide or antibody (including an antibody fragment) that specifically binds to a predetermined polymorphic region (or a specific region flanking the polymorphism), or a binding agent as defined herein. The product may additionally comprise one or more additional reagents or instruments (as are known in the art). The test kit would also include printed or machine-readable instructions setting forth the correlation between the presence of a specific polymorphism or genotype and the likelihood that a subject with asthma will respond favorably to therapy with a leukotriene receptor antagonist.

The invention provides a method for screening a subject diagnosed with asthma potentially treatable by leukotriene receptor antagonists, to determine the likelihood they will respond in a particular way to treatment with such a drug, more particularly a CysLT1 leukotriene receptor antagonist and most particularly zafirlukast. The method comprises screening the subject for a polymorphism in the ALOX5 gene and/or the LTC4S gene that has previously been associated with a high or low incidence of a particular desirable therapeutic outcome (compared to the incidence in subjects with other genotypes). Subjects are mammalian, and preferably humans.

Treatment of a subject with a leukotriene receptor antagonist comprises administration of an effective amount of the pharmaceutical agent to a subject in need thereof. The dose of agent is determined according to methods known and accepted in the pharmaceutical arts, and can be determined by those skilled in the art. A suitable dosage range for zafirlukast are provided in the disclosure of the Physician's Desk Reference, the entire disclosure of which is hereby incorporated herein by reference.

Genetic testing (also called genetic screening or genotyping) can be defined broadly as analyzing the nucleic acid of a subject to determine if the subject carries mutations (or alleles or polymorphisms) that are either (a) associated with, or causative of, a particular clinical phenotype, or (b) that are in 'linkage disequilibrium' with a mutation, allele or polymorphism that is associated with or causative of a particular clinical phenotype. One such clinical phenotype is the likelihood that the subject will respond favorably to a given therapeutic treatment.

Linkage disequilibrium refers to the tendency of specific alleles to occur together more frequently than would be expected by chance. Alleles at given loci are in equilibrium if the frequency of any particular set of alleles (or haplotype) is the product of their individual population frequencies. Disequilibrium may be due to various forces, including selection for certain allele combinations, or a recent mixing of genetically heterogeneous populations. Where markers link tightley to a disease-causing gene, an association of an allele (or a group of linked alleles) with the disease gene is expected if the disease mutation occurred in the recent historical past, so that sufficient time has not elapsed for equilibrium to be achieved through recombination events in the immediate chromosomal region.

The term 'marker,' as used herein, refers to a specific site in the genome which exhibits sequence variations among individuals.

The term 'allele' refers to the different sequence variants found at given markers. The sequence variants may be single or multiple base changes, including insertions, deletions or substitutions or may be variable number of sequence repeats and the like.

The term 'linkage disequilibrium' refers to the co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. Alleles that co-occur at expected frequencies are said to be in 'linkage equilibrium.' It will be apparent to those skilled in the art that the present methods may be carried out with polymorphisms that are in linkage disequilibrium with the specific polymorphisms identified herein.

The term 'haplotype' is a set of alleles that are inherited together as a group (i.e., that are in linkage disequilibrium). It will be apparent to those skilled in the art that the present methods may be utilized as a component of testing for haplotypes that encompass the polymorphisms described herein.

EXAMPLES

Example 1

Effects of Polymorphisms in the Promoter Region of 5-Lipoxygenase and LTC4 Synthase on the Clinical Response (Phenotypic Response) to Zafirlukast and Fluticasone Asthma subjects were genotyped by two distinct polymorphisms in the promoter regions of 5-lipoxygenase (ALOX5) and LTC4 synthase (LTC4S) genes. The polymorphisms were: the number of Sp1 repeats (n=3, 4, 5 or 6) in the approximate region of 176 to 147 base pairs upstream from the ATG start site in ALOX5 (Sp1), and an adenine to cytosine transversion 444 nucleotides upstream from the first codon in LTC4S (A-444C). Genomic DNA was isolated from blood samples obtained from consenting subjects participating in a 12 week multicenter, randomized, double-blind, double-dummy, parallel study comparing inhaled fluticasone (88 mcg BID) and oral zafirlukast (20 mg BID). Genomic DNA was extracted using standard procedures (automated extraction or using kit formats). The genotypes of the subjects, and any control individuals utilized, were determined for polymorphisms within the ALOX5 or LTC4S gene sequences. Polymorphisms are identifiable using PCR, PCR-RFLP, Taqman allelic discrimination assays, or any other suitable technique as is known in the art. If a specific polymorphism resides in an amplification product that is of sufficient physical size (e.g., an insertion/deletion polymorphism of multiple bases), a simple size discrimination assay can be employed to determine the genotype of an individual. In this case, two primers are employed to specifically amplify the gene of interest in a region surrounding the site of the polymorphism. PCR amplification is carried out, generating products which differ in length, dependent on the genotype (insertion or deletion) they possess. When subjected to gel electrophoresis, the differently sized products are separated, visualized, and the specific genotypes interpreted directly.

PCR-RFLP (polymerase chain reaction—restriction fragment length polymorphism) assays may also be utilized as is known in the art to detect polymorphisms. For each polymorphic site, a PCR-RFLP assay employs two gene-specific primers to anneal to, and specifically amplify a segment of genomic DNA surrounding the polymorphic site of interest. Following PCR amplification, specific restriction endonuclease enzymes are employed to digest the PCR products produced. The enzyme utilized for an assay is selected due to its specific recognition sequence which it requires to bind to, and cleave the PCR product in the presence/absence of the polymorphism, yielding fragments diagnostic of the specific base present at the polymorphic site. Following cleavage by the restriction enzyme, gel electrophoresis is employed to separate and visualize the fragments produced.

Taqman assays, as are known in the art, may also be utilized to identify polymorphisms. For each polymorphic site the allelic discrimination assay uses two allele specific probes labeled with a different fluorescent dye at their 5' ends but with a common quenching agent at their 3' ends. Both probes have a 3' phosphate group so that Taq polymerase cannot add nucleotides to them. The allele specific probes comprising the sequence encompassing the polymorphic site and will differ only in the sequence at this site (this is not necessarily true, the allele-specific probes can be shifted relative to each other such that they are not identical in length or composition. However, where they cover the same DNA region they are identical apart from the polymorphic site of interest). The allele specific probes are only capable of hybridizing without mismatches to the appropriate site.

The allele specific probes are used in conjunction with two primers, one of which hybridizes to the template 5' of the two specific probes, whilst the other hybridizes to the template 3' of the two probes. If the allele corresponding to one of the specific probes is present, the specific probe will hybridize perfectly to the template. The Taq polymerase, extending the 5' primer, will then remove the nucleotides from the specific probe, releasing both the fluorescent dye and the quenching agent. This will result in an increase in the fluorescence from the dye no longer in close proximity to the quenching agent.

If the allele specific probe hybridizes to the other allele the mismatch at the polymorphic site will inhibit the 5' to 3' endonuclease activity of Taq and hence prevent release of the fluorescent dye.

The AB17700 sequence detection system is used to measure the increase in the fluorescence from each specific dye at the end of the thermal cycling PCR directly in PCR reaction tubes. The information from the reactions is then analyzed. If an individual is homozygous for a particular allele only fluorescence corresponding to the dye from that specific probe will be released, but if the individual is heterozygous, then both dyes will fluoresce.

Primers and probes used in the present studies were as follows:

```
                                         (SEQ ID NO:6)
ALOX5 forward      AGGAACAGAC ACCTCGCTGA GGAGAG
primer:

(SEQ ID NO:7)
ALOX5 reverse      GAGCAGCGAG CGCCGGGAGC CTCGGC
primer:

(SEQ ID NO:8)
LTC4S-444A probe:  CCTGGATGGG GACAGGGAAC AG (SEQ ID NO:9)
LTC4S-444C probe:  TGGATGGGGA CCGGGAACAG (SEQ ID NO:10)
LTC4S forward      TCCGCAGAGG AGGGTTTG
primer:

(SEQ ID NO:11)
LTC4S reverse      GCTAACTCCT CCACCCACC T T
primer:
```

Figure 2:
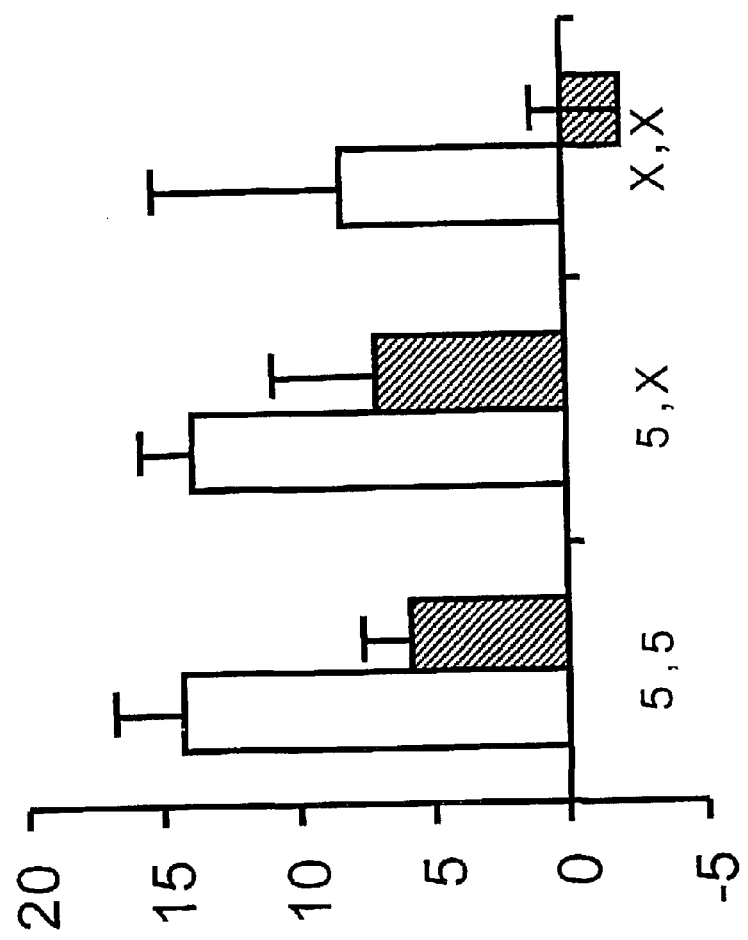
FIG. 2 is a graph showing the correlation between Sp1 polymorphisms at the ALOX5 gene and response to the leukotriene inhibitor compound zafirlukast, also showing the relative difference in such response as compared to fluticasone propionate (FP88). The vertical axis graphs the change in baseline $FEV_1$ (% predicted, change from baseline) after drug treatment; the horizontal axis provides genotypes (5,5= homozygous wildtype; 5,X=heterozygous wildtype; X,X= two non-wildtype alleles); open bars represent fluticasone propionate; shaded bars represent zafirlukast. Of the subjects, 88 (59.5%) had genotype 5,5 and 44 each were treated with FP88 and zafirlukast; 50 (33.8%) were 5,X (31 treated with FP88 and 19 treated with zafirlukast); and 10 (6.8%) were X,X (5 treated with FP88 and 5 treated with zafirlukast).
Figure 3:
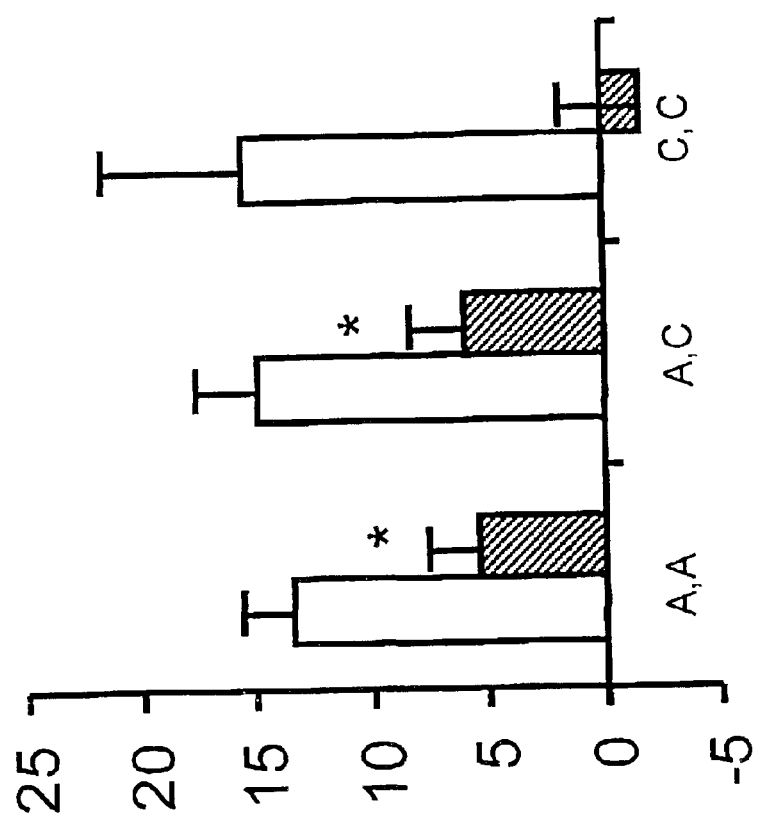
FIG. 3 is a graph showing the correlation between polymorphisms at the A-444C site in the LTC4 Synthase gene and response to the leukotriene inhibitor compound zafirlukast, also showing response to fluticasone propionate (FP88). The vertical axis graphs the change in baseline $FEV_1$ (% predicted, change from baseline) after drug treatment; the horizontal axis provides genotypes (A/A= homozygous wildtype; A/C=heterozygous wildtype; C/C= homozygous for adenine to cytosine transversion polymorphism); open bars represent fluticasone propionate; shaded bars represent zafirlukast. Asterisks indicate a significant difference ($p \leq 0.05$) between FP88 and zafirlukast results within a genotype. Of the subjects, 82 (57.8%) were A,A (48 treated with FP88, 34 treated with zafirlukast), 50 (35.2%) were A,C (20 treated with FP88, 30 treated with zafirlukast), 10 (7%) were C,C (6 treated with FP88, 4 treated with zafirlukast).
Figure 4:
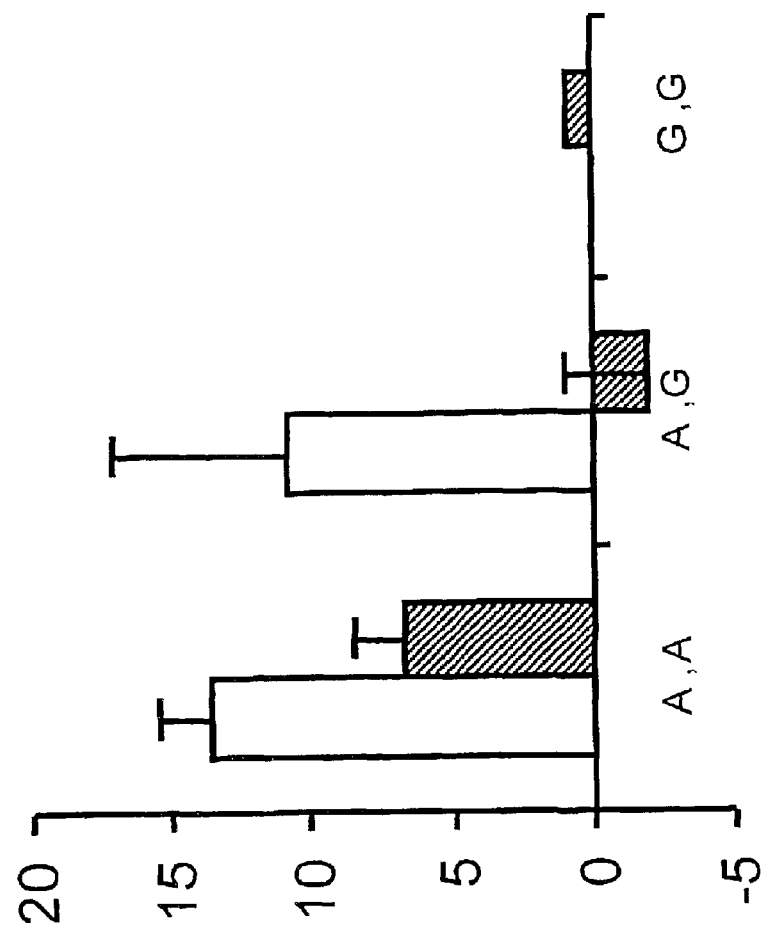
FIG. 4 is a graph showing the correlation between A1728G polymorphisms in the ALOX5 gene and response to fluticasone proprionate (FP88) and zafirlukast. The vertical axis represents the change in baseline $FE_1$ (% predicted, change from baseline) after drug treatment; the horizontal axis provides genotypes (A/A=homozygous wildtype; A/G= heterozygous wildtype; G/G=homozygous for adenine to guanine transversion polymorphism); open bars represent fluticasone propionate; shaded bars represent zafirlukast. Of the subjects, 130 were A,A (72 treated with FP88, 58 treated with zafirlukast), 18 were A,G (8 treated with FP88, 10 treated with zafirlukast), and 1 was G,G (treated with zafirlukast).

All patients met the ATS American Thoracic Society criteria for asthma, had a baseline forced expiratory volume ($FEV_1$) between 50 and 80% predicted, increased FEV1 by ≧12% following 180 mcg of inhaled albuterol, and had not used inhaled or oral steroids within 6 months of screening. The endpoint predose a.m. $FEV_1$ results (given in the table below as a % predicted change from baseline) by genotype and by treatment are presented below in Table 1 (see also FIG. 2 for ALOX5; FIG. 3 for LTC4S):

TABLE 1

| | ALOX5 Sp1 | | | LTC4S A-444C | | |
|---|---|---|---|---|---|---|
| | 5,5 | 5,X | X,X | A/A | A/C | C/C |
| Fluticasone | 14.2 ± 2.7 | 13.8 ± 2.0 | 8.3 ± 6.9 | 13.3 ± 2.3 | 14.8 ± 2.8 | 15.3 ± 6.2 |
| | n = 44 | n = 31 | n = 5 | n = 49 | n = 20 | n = 7 |

TABLE 1-continued

|  | ALOX5 Sp1 | | | LTC4S A-444C | | |
| --- | --- | --- | --- | --- | --- | --- |
|  | 5,5 | 5,X | X,X | A/A | A/C | C/C |
| Zafirlukast | 5.9 ± 1.8* | 7.1 ± 3.8 | −2.0 ± 3.2 | 5.3 ± 2.3* | 5.9 ± 2.3* | −1.8 ± 3.6 |
|  | n = 44 | n = 19 | n = 5 | n = 34 | n = 30 | n = 4 |

*= Significantly different from fluticasone
Where:
A is the wildtype polymorphic form of the LTC4S gene promoter region.
C is the variant polymorphic form of the LTC4S gene promoter region described in the Specification above.
5 is the wildtype polymorphic form of the ALOX5 gene promoter region.
X is the variant polymorphic form of the ALOX5 gene promoter region described in the specification above.
n is the number of test subjects.

None of the subjects who were homozygous variant at ALOX5 (X/X) were also homozygous variant for LTC4 (C/C). Some subjects were homozygous variant for one gene and heterozygous variant for the other, and others were heterozygous variant for both genes.

The results indicate that subjects homozygous for variants in the promoter region of either ALOX5 (X,X), or LTC4X (C/C), have a greatly reduced response to the leukotriene receptor antagonist zafirlukast compared to the other genotypes. These genes encode enzymes active in the biosynthesis of sulfidopeptide leukotrienes. The response to fluticasone 88 mcg BID was greater than to zafirlukast 20 mg BID across all genotypes. These results indicate a genetic basis for some of the variability observed in the clinical efficacy of the leukotriene receptor antagonist zafirlukast.

For ALOX5, it was found that 59.5% of the patients were homozygous wild type, 33.8% were heterozygous, and 6.8% were homozygous variant. These values are consistent with Drazen et al. who found frequencies of 56.1%, 35.1% and 8.8% for ALOS5 homozygous wild type, heterozygous and homozygous variant respectively. The frequencies for the LTC4S gene were 50.0%, 44.1% and 5.90% for wild type homozygous, heterozygous and homozygous variant, respectively. These values are similar to reported values of 43.2, 50.5 and 6.3%, respectively (Sanar, M. et al. The Lancet 1997; 350: 1599–1600).

Example 2

ALOX5 Polymorphisms at Nucleotide Positions 1728 and 1708 Response to Zafirlukast and Fluticasone The A to G transversion polymorphism at position 1728 in exon 13 of the ALOX5 gene, and the G to A transversion polymorphism at position-1708, were studied for any association with the FEV1 response to zafirlukast, compared to the inhaled glucocorticoid fluticasone. Both polymorphisms are set forth in In, KH et al., *J. Clin. Investigation* 99 (5):1130 (1997), the entire disclosure of which is incorporated herein by reference.

Genotyping was carried out on subjects with asthma participating in a 12 week randomized, double blind, parallel study of fluticasone (88 mcg BID) and the leukotriene receptor antagonist zafirlukast (20 mg BID). Predose FEV1 results (change from baseline in percent predicted) are shown in Table 3.

TABLE 3

|  | Fluticasone | Zafirlukast |
| --- | --- | --- |
| Genotype G1708A | | |
| G/G | 15.0 ± 2.3 | 4.7 ± 1.9* |
|  | n = 50 | n = 46 |
| G/A | 12.7 ± 2.3 | 8.5 ± 3.5 |
|  | n = 26 | n = 18 |
| A/A | — | 0.7 ± 2.2 |
|  | n = 0 | n = 4 |
| Genotype A1728G | | |
| A/A | 13.6 ± 1.8 | 6.8 ± 1.7 |
|  | n = 72 | n = 58 |
| A/G | 10.8 ± 6.3 | −1.9 ± 2.9 |
|  | n = 8 | |
| G/G | — | 0.8 |
|  | n = 0 | n = 1 |

*= significant difference between zafirlukast and fluticasone

The above results suggest that subjects homozygous for the A allele at the 1708 site (G1708A), or who have one or two G alleles at the 1728 site (A1728G), had reduced response to zafirlukast, compared to alternative genotypes. This result did not reach statistical significance, possibly due to low sample number.

The G1708A promoter polymorphism was in significant Linkage Disequilibrium (LD) with the Sp1 promoter marker that alters efficacy. The A1728G polymorphism was not in LD with the Sp1 site and therefore may be affecting clinical response independently. The frequency of the G and A alleles for 1708 are 0.82 and 0.18 respectively, and the A and G alleles for 1728 are 0.93 and 0.07 respectively. Both are in Hardy Weinberg equilibrium. These results suggest that variability in clinical response to zafirlukast may be associated with multiple genetic polymorphisms in the leukotriene pathway.

That which is claimed is:

1. A method of screening a subject suffering from asthma, as an aid in predicting their response to treatment with a leukotriene receptor antagonist ligand, comprising:
   a) obtaining a sample of DNA from the subject; and
   b) genotyping said DNA sample in the 5' non-coding region of the LTC$_4$ Synthase (LTC4S) gene for the presence of SEQ ID NO:3 or SEQ ID NO:4;

wherein homozygosity for an allele comprising SEQ ID NO:4 indicates that the subject is less likely to respond favorably to treatment with a leukotriene receptor antagonist for asthma, compared to a subject having an allele comprising SEQ ID NO:3.

2. A method according to claim 1 where said leukotriene receptor antagonist ligand is a cysteinyl leukotriene 1 (CysLT1) receptor antagonist.

3. A method according to claim 1 where said leukotriene receptor antagonist ligand is selected from the group consisting of zafirlukast, pranlukast, iralukast and montelukast.

4. A method of identifying, within a population of asthma patients, a subpopulation of asthma patients with an increased likelihood of responding favorably to therapy with a leukotriene receptor antagonist, comprising the step of:

(a) obtaining a DNA sample from each of said subjects; and;

(b) conducting on each DNA sample a genotyping test selected from (i) determining the number of repeats of SEQ ID NO:12 in the 5' noncoding region of the ALOX5 gene, and (ii) determining whether the 5' non-coding region of the $LTC_4$ Synthase (LTC4S) gene is homozygous for an allele comprising SEQ ID NO:4 or contains an allele comprising SEQ ID NO:3;

wherein the subpopulation of asthma patients with an increased likelihood of responding favorably to treatment with a leukotriene receptor antagonist consists of subjects with an ALOX5 allele having five repeats of SEQ ID NO:12 or having at least one LTC4S allele comprising SEQ ID NO:3.

5. A method according to claim 4 where said leukotriene receptor antagonist ligand is a cysteinyl leukotriene 1 (CysLT1) receptor antagonist.

6. A method according to claim 4 where said leukotriene receptor antagonist ligand is selected from the group consisting of zafirlukast, pranlukast, iralukast and montelukast.

* * * * *